US012767961B2

(12) United States Patent
Lee et al.

(10) Patent No.: US 12,767,961 B2
(45) Date of Patent: Oct. 20, 2026

(54) METHOD FOR SINGLE-BASE GENOME EDITING USING CRISPR/CPF1 SYSTEM AND USES THEREOF

(71) Applicant: CHUNG ANG UNIVERSITY INDUSTRY ACADEMIC COOPERATION FOUNDATION, Seoul (KR)

(72) Inventors: Sang Jun Lee, Gyeonggi-do (KR); Ho Joung Lee, Gyeonggi-do (KR); Hyun Ju Kim, Gyeonggi-do (KR)

(73) Assignee: CHUNG ANG UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 89 days.

(21) Appl. No.: 17/727,142

(22) Filed: Apr. 22, 2022

(65) Prior Publication Data

US 2022/0340934 A1 Oct. 27, 2022

(30) Foreign Application Priority Data

Apr. 22, 2021 (KR) ........................ 10-2021-0052619
Apr. 21, 2022 (KR) ........................ 10-2022-0049739

(51) Int. Cl.
*C12N 15/90* (2006.01)
*C12N 15/11* (2006.01)

(52) U.S. Cl.
CPC ............ *C12N 15/902* (2013.01); *C12N 15/11* (2013.01); *C12N 2310/20* (2017.05)

(58) Field of Classification Search
CPC .. C12N 15/902; C12N 15/11; C12N 2310/20; C12N 15/113; C12N 15/90
See application file for complete search history.

(56) References Cited

U.S. PATENT DOCUMENTS

2020/0291368 A1 9/2020 Van Der Oost et al.
2020/0308583 A1 10/2020 Kim et al.

OTHER PUBLICATIONS

Kleinstiver BP, Tsai SQ, Prew MS, Nguyen NT, Welch MM, Lopez JM, McCaw ZR, Aryee MJ, Joung JK. Genome-wide specificities of CRISPR-Cas Cpf1 nucleases in human cells. 2016. Nat Biotechnol. Aug. 2016;34(8):869-74. doi: 10.1038/nbt.3620. (Year: 2016).*

Hur, J., Kim, K., Been, K. et al. Targeted mutagenesis in mice by electroporation of Cpf1 ribonucleoproteins. 2016. Nat Biotechnol 34, 807-808 (2016). doi: 10.1038/nbt.3596 (Year: 2016).*

Gaudelli NM, Komor AC, Rees HA, Packer MS, Badran AH, Bryson DI, Liu DR. Programmable base editing of A•T to G•C in genomic DNA without DNA cleavage. 2017. Nature. Nov. 23, 2017;551(7681):464-471. doi: 10.1038/nature24644 (Year: 2017).*

Kleinstiver BP, Tsai SQ, Prew MS, Nguyen NT, Welch MM, Lopez JM, McCaw ZR, Aryee MJ, Joung JK. Genome-wide specificities of CRISPR-Cas Cpf1 nucleases in human cells. 2016. Supplementary Figure 1. (Year: 2016).*

Kleinstiver BP, Tsai SQ, Prew MS, Nguyen NT, Welch MM, Lopez JM, McCaw ZR, Aryee MJ, Joung JK. Genome-wide specificities of CRISPR-Cas Cpf1 nucleases in human cells. 2016. Supplementary Figure 3. (Year: 2016).*

Yan M, Yan H, Ren G, Zhao J, Guo X, Sun Y.2017.CRISPR-Cas 12a-Assisted Recombineering in Bacteria. Appl Environ Microbiol83:e00947-17.https://doi.org/10.1128/AEM.00947-17 (Year: 2017).*

Kim, H. J.; Oh, S. Y.; Lee, S. J. Single-base genome editing in Corynebacterium glutamicum with the help of negative selection by target-mismatched CRISPR/Cpf1. J. Microbiol. Biotechnol. 2020, 30, 1583-1591, DOI: 10.4014/jmb.2006.06036 3 (Year: 2020).*

Kleinstiver (Nat Biotechnol, 2016, vol. 34, No. 8, Supplementary Fig. 3C) (Year: 2016).*

Zetsche et al. (Cell Oct. 22, 2015, 163:759-771) (Year: 2015).*

Yu Jiang, et al., "CRISPR-Cpf1 assisted genome editing of Corynebacterium glutamicum", nature communications, May 4, 2017.

Mei-Yi Yan, et al., "CRISPR-Cas12a-Assisted Recombineering in Bacteria", American Society for Microbiology, Applied and Environmental Microbiology, Jun. 23, 2017, vol. 83, Issue 17.

Hyo Min Park, et al. "Extension of the crRNA enhances Cpf1 gene editing in vitro and in vivo", nature communications, 2018.

Xuhua Zhang, et al. "Genetic editing and interrogation with Cpf1 and caged truncated pre-tRNA-like crRNA in mammalian cells", Cell Discovery, 2018.

Su Bin Moon, et al. "Highly efficient genome editing by CRISPR-Cpf1 using CRISPR RNA with a uridinylate-rich 3'-overhang", nature communications, 2018.

* cited by examiner

*Primary Examiner* — Peter J Reddig
(74) *Attorney, Agent, or Firm* — Vorys, Sater, Seymour and Pease LLP; Mih Suhn Koh

(57) ABSTRACT

The present disclosure relates to a method of editing a genome based on the CRISPR/Cpf1 system and a use thereof, and the CRISPR system using an oligonucleotide-induced mutation and 3'-truncated crRNA according to the present disclosure provides the significant effect of genome editing to the target DNA.

5 Claims, 17 Drawing Sheets

Specification includes a Sequence Listing.

FIG. 2

Unedited (*galK* 497-517)

PAM

SEQ ID NO: 42 TTG TAGGCTGTAACTGCGGGATCA

Single base edited ($^{504}$T → A)

SEQ ID NO: 43 1. TTG TA-GGCTGAAACTGCGGGATCA
SEQ ID NO: 44 2. TTG TA-GGCTGAAAC GG ATCA
SEQ ID NO: 45 3. TTG T -GGCTGAAACTGCGGGATCA
SEQ ID NO: 46 4. TTG TA-G CTGAAACTGCGGGATCA
SEQ ID NO: 47 5. TTG TA-GGC GAAACTGCGGGATCA
SEQ ID NO: 48 6. TTG TA-GGCTGAAACT CGGGATCA
SEQ ID NO: 49 7. TTG TA-GGC GAAACTGCGGGATCA
SEQ ID NO: 50 8. TTG T -GGCTGAAACTGCGGGATCA
SEQ ID NO: 51 9. TTG TA-G CTGAAACTGCGGGATCA
SEQ ID NO: 52 10. TTG TA GGCTGAAACTGCGGGATCA

Double bases edited ($^{504}$TA → AT)

SEQ ID NO: 53 1. TTG TAGGCTGATACTGCGGGATCA
SEQ ID NO: 53 2. TTG TAGGCTGATACTGCGGGATCA
SEQ ID NO: 53 3. TTG TAGGCTGATACTGCGGGATCA
SEQ ID NO: 53 4. TTG TAGGCTGATACTGCGGGATCA
SEQ ID NO: 53 5. TTG TAGGCTGATACTGCGGGATCA

Triple bases edited ($^{503}$GTA → AGC)

SEQ ID NO: 54 1. TTG TAGGCTAGCACTGCGGGATCA
SEQ ID NO: 54 2. TTG TAGGCTAGCACTGCGGGATCA
SEQ ID NO: 54 3. TTG TAGGCTAGCACTGCGGGATCA
SEQ ID NO: 54 4. TTG TAGGCTAGCACTGCGGGATCA
SEQ ID NO: 54 5. TTG TAGGCTAGCACTGCGGGATCA

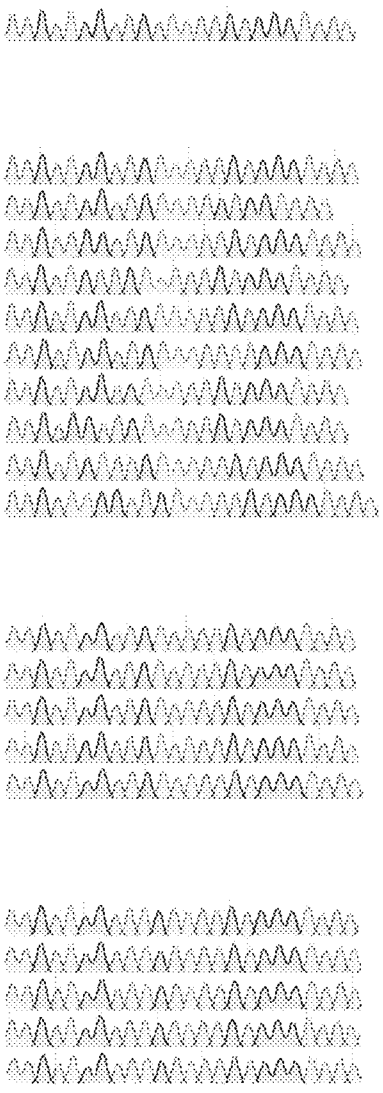

*galK*

*xylB*

METHOD FOR SINGLE-BASE GENOME EDITING USING CRISPR/CPF1 SYSTEM AND USES THEREOF

CROSS-REFERENCE TO RELATED APPLICATIONS

This application is based on and claims priority from Korean Patent Application No. 10-2021-0052619, filed on Apr. 22, 2021 and Korean Patent Application No. 10-2022-0049739, filed on Apr. 21, 2022, with the Korean Intellectual Property Office, the disclosure of which is incorporated herein in its entirety by reference.

The contents of the electronic sequence listing (Sequence-Listing.txt; Size: 15,097 bytes; and Date of Creation: Jun. 4, 2025) is herein incorporated by reference in its entirety.

TECHNICAL FIELD

The present disclosure relates to a method for single-base genome editing using a CRISPR/Cpf1 system and a use thereof.

BACKGROUND

The clustered regularly interspaced short palindromic repeats (CRISPR) system is an adaptive immune system of microorganisms in which, after being infected with foreign DNA such as bacteriophage, the surviving microorganism stores a part of the infected DNA sequence in the form of a spacer, recognizes it when re-infected and causes double-strand breaks in the invading DNA. The function of the CRISPR system is modularized with a crRNA portion that recognizes the target DNA and a Cas protein with nuclease activity that causes double-strand breaks by approaching the target via crRNA and is used as a genome editing tool to create mutations in the genomes of various microorganisms, with its modularity being used to its advantage. CRISPR is divided into various classes and types depending on the number and type of Cas proteins. Among them, the CRISPR/Cas (CRISPR-associated) system belonging to Class II consists of a single polypeptide with Cas nuclease that causes double-strand breaks in target DNA, and it has been most actively studied among the CRISPR systems.

In addition to the base pairing of crRNA and target DNA to induce double-strand breaks at the target site, the CRISPR system requires interaction between the protospacer adjacent motif (PAM) and Cas nuclease present in the sequence immediately adjacent to the target site. A PAM is a short sequence that is immediately adjacent to a target site. Among CRISPR/Cas, Cas9, which has been studied the most, has a PAM sequence of 5'-NGG. PAM is an important criterion for distinguishing foreign DNA from self DNA in the CRISPR system. Since it requires a specific nucleotide sequence, it also acts as an obstacle that limits the range of sites that may be selected as targets in the genome. Therefore, CRISPR/Cas systems with PAMs of various sequences have been studied to broaden the range of targets that can be selected.

One of them, the CRISPR from Prevotella and Francisella 1 (CRISPR/Cpf1) system belongs to CRISPR Class II because the Cpf1 nuclease consists of a single polypeptide. To form the Cas nuclease/gRNA complex, only crRNA is required to form the Cpf1/gRNA complex, unlike Cas9, which additionally requires tracrRNA in addition to crRNA. In addition, *Francisella novicida*-derived FnCpf1 has a PAM sequence of 5'-TTTN, which can target a T-rich region that Cas9 cannot target, thereby further reducing the restrictions of PAM.

In genome editing of microorganisms using Cpf1, as in Cas9, cells in which the target site is not mutated are recognized as targets by CRISPR/Cpf1 and die due to double-strand breaks in the cell genome, and cells with mutations in the target DNA sequence by oligonucleotide-directed mutagenesis are not recognized as a target, so they survive and are made through negative selection to obtain a mutated strain.

Currently, studies on editing the genome of microorganisms using the CRISPR/Cpf1 system in the case in which it is impossible to edit with Cas9 are being actively conducted. The present inventors reported that even if the target DNA sequence and the target recognition sequence of sgRNA do not all match in CRISPR/Cas9, it is difficult to introduce single base mutations due to mismatch tolerance that causes double-strand breaks. It was confirmed that the mismatch tolerance of the CRISPR/Cas9 system, which recognizes and kills a target with a point mutation of 1 to 2 bases identically as a target with no mutation, is also occurred in Cpf1. In addition, there was a problem in that point mutations were induced at the desired site with low efficiency even using CRISPR/Cpf1 for the above reasons.

Therefore, there is a need for research on a method that can overcome these obstacles and freely and efficiently edit the target genome including microorganisms.

PRIOR ART LITERATURE

Patent Literature (Patent Document 1) US Patent Publication No. 20200291368A1 (published on Sep. 17, 2020)

(Patent Document 2) Korea Patent Publication No. 10-2018-0144185 (published on May 29, 2019)

Non-Patent Literature (Non-Patent Document 1) Jiang, Y., Qian, F., Yang, J., Liu, Y., Dong, F., Xu, C., Sun, B., Chen, B., Xu, X., Li, Y., Wang, R., Yang, S., 2017. CRISPR-Cpf1 assisted genome editing of Corynebacterium glutamicum. Nat. Commun. 8, 15179.

(Non-Patent Document 2) Yan, M. Y., Yan, H. Q., Ren, G. X., Zhao, J. P., Guo, X. P., Sun, Y. C., 2017. CRISPR-Cas12a-Assisted Recombineering in Bacteria. AppL Environ. Microbiol. 83.

SUMMARY

Under such circumstances, the present inventors have made intensive studies to develop a method capable of precisely editing a target genome at the level of a single base based on a CRISPR/Cpf1 system. Accordingly, the present inventors have designed the incorporation of a site-directed mutation using an oligonucleotide containing a nucleotide sequence that is not perfectly complementary to the target DNA, into the CRISPR/Cpf1 system including modified crRNAs with its 3'-end nucleotide truncations, which is homologous to the target DNA. As a result, where 5 nucleotides in the crRNA are truncated (deleted) at the 3'-end thereof, thereby overcoming the mismatch tolerance of the CRISPR/Cpf1 system and accurately editing the *E. coli* genome to a single base level as well as identifying that the point mutation incorporation efficiency is improved, so that the present disclosure has been completed.

Therefore, an object of the present disclosure is to provide a genome editing method based on the CRISPR/Cpf1 system.

In addition, another object of the present disclosure is to provide a method for increasing genome editing efficiency based on the CRISPR/Cpf1 system.

In addition, still another object of the present disclosure is to provide a method for preparing a subject in which the target DNA has been edited based on the CRISPR/Cpf1 system.

Other objects and advantages of the present disclosure become more apparent by the following detailed description and claims.

The terms used herein are used for the purpose of description only, and should not be construed as limiting. The singular expression includes the plural expression unless the context clearly dictates otherwise. In the present specification, it is to be understood that terms such as "comprise" or "have" are intended to designate that a feature, number, step, operation, component, part, or a combination thereof described in the specification exists, but this does not preclude the possibility of addition or existence of one or more other features, numbers, steps, operations, components, parts, or combinations thereof.

In addition, unless otherwise defined, all terms used herein, including technical or scientific terms, have the same meaning as commonly understood by those of ordinary skill in the art to which the embodiment belongs. Terms such as those defined in a commonly used dictionary should be interpreted as having a meaning consistent with the meaning in the context of the related art. Unless explicitly defined herein, it should not be construed in an ideal or overly formal sense.

As used herein, the terms "nucleic acid sequence," "nucleotide sequence," and "polynucleotide sequence" refer to oligonucleotides or polynucleotides, and fragments or portions thereof, and DNA of genomic or synthetic origin, which may be single-stranded or double-stranded, or RNA, and represents the sense or antisense strand.

Hereinafter, the present disclosure is described in detail.

In one aspect of the present invention, there is provided a method for single-base genome editing based on clustered regularly interspaced short palindromic repeats/CRISPR from prevotella and francisella 1 (CRISPR/Cpf1) system, comprising crRNA (CRISPR RNA) and a donor nucleic acid molecule that complementarily binds to a target DNA, the method comprises step of preparing a 3'-truncated crRNA in which 1 to 5 nucleotides are truncated from the 3'-end of the crRNA comprising a nucleotide sequence complementary to the target DNA.

As used herein, the terms "edit," "editing," or "edited" refer to a method of altering a nucleic acid sequence of a polynucleotide (e.g., a wild-type naturally occurring nucleic acid sequence or a mutated naturally occurring sequence) by selectively deleting a specific genomic target or incorporating a new specific sequence using an externally supplied DNA template. Such specific genomic targets may include, but are not limited to, chromosomal regions, mitochondrial DNA, genes, promoters, open reading frames, or any nucleic acid sequence.

As used herein, the term "genome editing," unless otherwise specified, refers to editing, restoring, modifying, losing and/or altering gene function by deletion, insertion, substitution, etc. of a nucleic acid molecule by Cpf1 cleavage at a target site of a target DNA.

As used herein, the terms "delete," "deleted," "deleting," or "deletion" are defined as a change in the nucleotide or amino acid sequence, respectively, that results in the absence (removal) or absence of one or more nucleotide or amino acid residues.

Preferably, in the present disclosure, a 3'-truncated crRNA means a crRNA in which 1 to 5 nucleotides are deleted (truncated) from the 3'-end of a crRNA including a nucleotide sequence complementary to the target DNA. The 3'-truncated crRNA comprises a region consisting of 16 to 20 consecutive nucleotides complementary to the target DNA, and this 3'-truncated crRNA is characterized in that it rather enhances the editing effect of the CRISPR system.

The number of deleted nucleotides is not limited as long as the object of the present disclosure may be achieved, but preferably, the number of deleted nucleotides is 1 to 10, more preferably 1 to 5, most preferably 5.

In addition, the deleted nucleotides on the crRNA may be continuously or discontinuously located.

According to the present disclosure, the position of the deleted nucleotide on the crRNA, that is, the 3'-truncated crRNA of the present disclosure, is immediately adjacent sites 1 to 5 nucleotides apart from the 3'-end on the crRNA.

As used herein, the term "immediately adjacent" when used to refer to the position of a deleted nucleotide on a 3-truncated crRNA means to be located at adjacent (juxtaposition), that is, spaced apart by 1 nucleotide, from the 3'-end direction on a crRNA including a nucleotide sequence complementary to the target DNA.

The term "crRNA" refers to an RNA specific for a target DNA, capable of forming a complex with a Cpf1 protein, and bringing the Cpf1 protein to the target DNA. Any crRNA may be used in the present disclosure as long as the crRNA contains a portion complementary to the target. The crRNA may hybridize with the target DNA.

The crRNA may be delivered to a cell or organism in the form of RNA or in the form of DNA encoding the crRNA. In addition, crRNA may be in the form of isolated RNA, RNA contained in a viral vector, or encoded in a vector. Preferably, the vector may be a viral vector, a plasmid vector, or an Agrobacterium vector, but is not limited thereto.

As used herein, the term "3'-truncated crRNA" used while referring to the CRISPR/Cpf1 system-based genome editing, refers to a crRNA in which some nucleotides are deleted from the 3'-end of a crRNA containing a nucleotide sequence complementary to a target DNA.

As used herein, the term "donor nucleic acid molecule" or "donor nucleic acid sequence" used while referring to CRISPR/Cas9 system-based genome editing, refers to a natural or modified polynucleotide including a nucleotide sequence intended to be inserted into a target DNA, RNA-DNA chimera, or DNA fragment, or PCR amplified ssDNA or dsDNA fragment or analog thereof.

Such a donor nucleic acid molecule may include any form, such as single-stranded and double-stranded form, as long as it may induce genetic modifications on the target DNA to achieve the purpose of the present disclosure.

Modifications on the target DNA may include a substitution of one or more nucleotides, an insertion of one or more nucleotides, a deletion of one or more nucleotides, a knockout, a knockin, a replacement of an endogenous nucleic acid sequence with a homologous or orthologous, or heterologous nucleic acid sequence, or a combination thereof at any desired position.

In the present disclosure, preferably, the modification on the target DNA is one in which a point mutation is introduced (induced) by substitution of one or more nucleotides in a wild-type DNA sequence, and the introduction of the point mutation is, for example, by an oligonucleotide.

As used herein, the term "hybridization" means that complementary single-stranded nucleic acids form double-stranded nucleic acids. Hybridization occurs when the complementarity between two nucleic acid strands has a perfect match or when some mismatched bases may also be present.

Cpf1 protein is a novel endonuclease of the CRISPR system that is distinct from the CRISPR/Cas system, and has a relatively small size compared to Cas9, does not require tracrRNA, and may be acted by a single guide RNA.

In addition, the Cpf1 protein recognizes a DNA sequence rich in thymine, such as 5'-TTN-3' or 5'-TTTN-3' (N is any nucleotide having a base of A, T, G or C) located at the 5' end as a PAM (protospacer-adjacent motif) sequence and cut the double-stranded DNA to create a cohesive end (cohesive double-strand break). The resulting cohesive end may facilitate NHEJ-mediated transgene knock-in at the target site (or cleavage site).

In the CRISPR/Cpf1 system of the present disclosure, the PAM is a 5'-TTN-3' base.

For example, the Cpf1 protein may be derived from *Candidatus* genus, *Lachnospira* genus, *Butyrivibrio* genus, *Peregrinibacteria, Acidominococcus* genus, *Porphyromonas* genus, *Prevotella* genus, *Francisella* genus, *Candidatus Methanoplasma*, or *Eubacterium* genus. For example, the Cpf1 protein may be derived from a microorganism of *Parcubacteria bacterium, Lachnospiraceae bacterium, Butyrivibrio proteoclasiicus, Peregrinibacteria bacterium, Acidaminococcus* sp., *Porphyromonas macacae, Lachnospiraceae bacterium, Porphyromonas crevioricanis, Prevotella disiens, Moraxella bovoculi, Smiihella* sp., *Leptospira inadai, Lachnospiraceae bacterium, Francisella novicida, Candidatus Methanoplasma termitum, Candidatus Paceibacter, Eubacterium eligens*, but is not limited thereto.

The target DNA includes nucleotides complementary to the crRNA and a protospacer-adjacent motif (PAM).

When a mutagenic oligonucleotide, which is the prior art, is inserted into a cell, the mutation is only introduced in a low yield in the process of DNA replication. Even when using the conventional CRISPR/Cpf1 system, it was difficult to introduce a single base point mutation due to the mismatch tolerance of CRISPR/Cpf1.

Accordingly, in order to solve the above problems, the present inventors introduced a site-directed mutation into an oligonucleotide containing a nucleotide sequence having a single base mismatch in the target DNA in the CRISPR/Cpf1 system including a 3'-truncated crRNA with some nucleotides deleted from the 3'-end.

As a result, the present inventors elucidated that a 3'-truncated crRNA with homology to the target DNA and 5 nucleotides deleted from the 3'-end overcomes the mismatch tolerance of the CRISPR/Cpf1 system to achieve the effect of greatly improving efficiency and accuracy of single base genome editing (repairing) using it.

Therefore, according to the method of the present disclosure, it is demonstrated that the genome of the target subject may be efficiently edited in a single base unit.

In addition, according to another aspect of the present invention, there is provided a composition for genome editing based on a CRISPR/Cpf1 system including a donor nucleic acid molecule that complementarily binds to a target DNA and crRNA (CRISPR RNA). The crRNA including a nucleotide sequence complementary to target DNA has 1 to 5 nucleotides truncated from 3'-end thereof.

According to one embodiment of the present disclosure, the composition of the present disclosure is characterized in that it recognizes a target gene in the CRISPR-Cpf1 system, but includes a construct capable of expressing a 3'-truncated crRNA, which is a crRNA having 1 to 5 nucleotides deleted from the selected target DNA sequence rather than the selected target DNA sequence, 3'-truncated crRNA and a donor DNA (e.g., oligonucleotide) are simultaneously delivered into a cell, and upon cleavage of the target DNA by Cpf1 protein, the donor DNA including the mutant sequence may be included in the genome instead of the target DNA through the donor DNA to increase the substitution mutation efficiency of the target DNA.

Since the composition of the present disclosure uses the method of the present disclosure described above, the overlapped content is excluded to avoid excessive complexity of the present specification.

In addition, according to still another aspect of the present invention, there is provided a method of increasing genome editing efficiency based on the CRISPR/Cpf1 system including a donor nucleic acid molecule that complementarily binds to a target DNA and crRNA, and the method comprises step of preparing a 3'-truncated crRNA in which 1 to 5 nucleotides are truncated from the 3'-end of the crRNA comprising a nucleotide sequence complementary to the target DNA.

Since the method of the present disclosure uses the method described above, the overlapped content is excluded to avoid the excessive complexity of the present specification.

In addition, according to still another aspect of the present invention, there is provided a method for preparing a subject in which a target DNA is edited based on the CRISPR/Cpf1 system, comprising the steps of:

(a) constructing a donor nucleic acid molecule that complementarily binds to the target DNA and induces modification on the target DNA;
(b) constructing a 3'-truncated crRNA in which 1 to 5 nucleotides are truncated from the 3'-end of the crRNA comprising a nucleotide sequence complementary to the target DNA; and
(c) contacting the donor nucleic acid molecule of step (a) and the 3'-truncated crRNA of step (b) into the subject to be edited, thereby editing the target DNA of the subject.

In addition, the CRISPR/Cpf1 system of the present disclosure may use any selectable marker known in the art, as long as it may achieve the purpose of the present disclosure.

The subject of the present disclosure is not limited as long as the method of the present disclosure is applicable, but may preferably be a plasmid, a virus, a prokaryotic cell, an isolated eukaryotic cell, or a eukaryotic organism other than a human.

The eukaryotic cells may be cells of yeast, fungus, plants, insects, amphibians, mammals, etc., and for example, may be cells cultured in vitro, transplanted cells, primary cell culture, in vivo cells, mammalian cells including human cells commonly used in the art, but is not limited thereto.

Any nucleic acid or Cpf1 protein encoding the Cpf1 protein may be used as long as it may achieve the purpose of the present disclosure.

According to still another aspect of the present invention, there is provided a target DNA-edited subject prepared by the above-described method for preparing the subject in which the target DNA is edited.

The present disclosure relates to a method of editing and repairing the genome of a target subject in a single base unit and has an effect of providing a method for producing a target subject with a mutation in the target gene, for example, a strain optimized for production ability of useful substances, etc. by correctly repairing the genome of microbial strains or by causing a codon change.

According to the exemplary embodiments of the present disclosure, the CRISPR system using oligonucleotide-induced mutagenesis and 3'-truncated crRNA according to the present disclosure provides a significant single-base genome editing effect on the target DNA, expecting that it may be used in a wide range of fields such as creating a commercial profit as an industrial strain with improved productivity, enhancing the quality of public health care by improving intestinal microbes, and improving crops and livestock breeds free from GMO issues.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 2 shows a Sanger sequence analysis result of a target site after base editing, indicating the inaccuracy of single base editing.

FIG. 5-Unedited (galK 497-517): SEQ ID No. 42, 510 C to A: SEQ ID No. 43; Unedited (xylB 637-657): SEQ ID No. 44; and 643 G to T: SEQ ID No. 45.

FIG. 6A—galK target: SEQ ID No. 46; and FIG. 6B—xylB target: SEQ ID No. 47.

FIG. 7 (galK)—G499 A: SEQ ID No. 48; G499 T: SEQ ID No. 49; G499 C: SEQ ID No. 50; C501 A: SEQ ID No. 51; G503 T: SEQ ID No. 52; G503 C: SEQ ID No. 53; T504 G: SEQ ID No. 54; T504 A: SEQ ID No. 55; T504 C: SEQ ID No. 56; A505 G: SEQ ID No. 57; A505 A: SEQ ID No. 58; A505 C: SEQ ID No. 59; A506 T: SEQ ID No. 60; T508 G: SEQ ID No. 61; T508 A: SEQ ID No. 62; T508 C: SEQ ID No. 63; C510 G: SEQ ID No. 64; C510 A: SEQ ID No. 65; and C510 T: SEQ ID No. 66.

FIG. 8 (xylB)—A639 G: SEQ ID No. 67; A639 T: SEQ ID No. 68; A639 C: SEQ ID No. 69; C640 A: SEQ ID No. 70; T642 G: SEQ ID No. 71; G646 C: SEQ ID No. 72; T648 G: SEQ ID No. 73; T648 C: SEQ ID No. 74; G649 T: SEQ ID No. 75; G649 C: SEQ ID No. 76; C650 A: SEQ ID No. 77; and C650 G: SEQ ID No. 78.

FIG. 10—510G insertion: SEQ ID No. 79; 509G deletion: SEQ ID No. 80; 510AG insertion: SEQ ID No. 81; 509GC deletion: SEQ ID No. 82; 643A insertion: SEQ ID No. 83; 643G deletion: SEQ ID No. 84; 643AG insertion: SEQ ID No. 85; and 643GA deletion: SEQ ID No. 86.

DETAILED DESCRIPTION

Figure 1A:
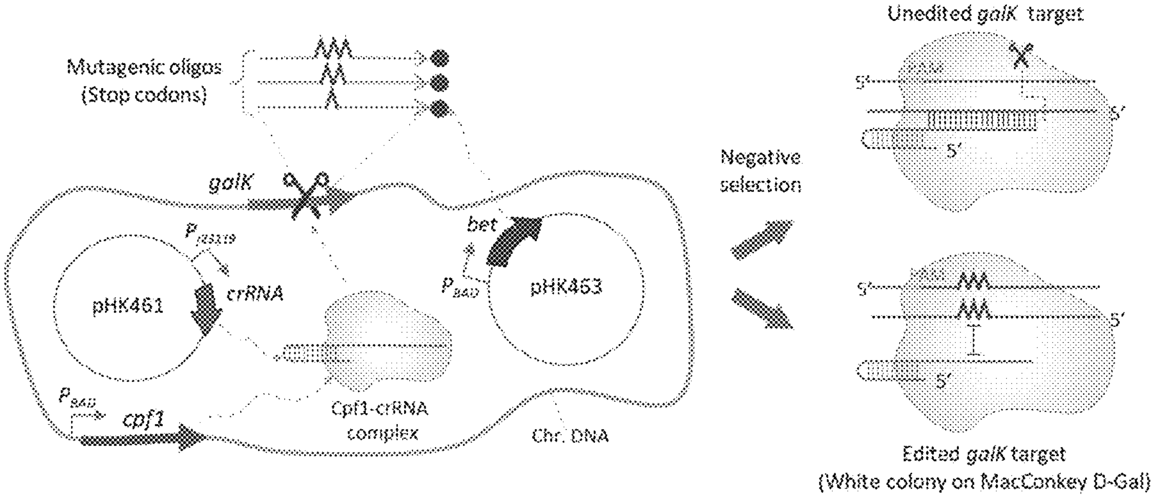
FIG. 1A shows a conceptual diagram of constructing a negative selection system using CRISPR/Cpfl.

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the examples are only for explaining the present disclosure in more detail, and it will be apparent to those of ordinary skill in the art to which the present disclosure belongs that the scope of the present disclosure is not limited by these embodiments according to the gist of the present disclosure.

Example 1. Construction of a Negative Selection System using CRISPR/Cpf1

The present inventors produced a mutant *E. coli* strain (*E. coli* MG1655 araBAD::$P_{BAD}$-cpf1-KmR) in which the Cpf1 gene is inserted into the genome through lambda-red recombineering. The *E. coli* MG1655 strain was spread on LB solid medium and a single colony grown was inoculated in 200 ml of LB liquid medium. They were cultured at 37° C. until $OD_{600\ nm}$ approached 0.4 and centrifuged at 3500 rpm for 20 minutes. They were washed with 40 ml of 10% glycerol twice to prepare electrocompetent cells.

The cpf1 gene to be inserted was PCR-amplified from pJYS1Ptac (Addgene plasmid #85545) and was amplified by PCR to be the cpf1-KmR cassette to have a homologous sequence for recombination together with the kanamycin gene. The amplified PCR product was purified and then inserted into *E. coli* MG1655 overexpressed with the lambda-red recombinase of the pKD46 plasmid by L-arabinose to be located at the back of the promoter in which the expression of the gene in L-arabinose is induced, thereby preparing the HK1061 strains.

After spreading the HK1061 strain on the LB solid medium, the grown single colonies were inoculated into 200 ml of the LB liquid medium and cultured at 30° C. until the $OD_{600\ nm}$ became 0.4. L-arabinose was added at a concentration of 1 mM and further cultured for 3 hours to overexpress the lambda-red beta protein and Cpf1 protein. After centrifugation at 3500 rpm for 20 minutes, washing with 40 ml of 10% glycerol was performed twice to prepare electrocompetent cells.

Thereafter, the lambda-red beta expression plasmid pHK463 to aid recombination by oligonucleotide was inserted into the HK1061 strain of Example 1. The single colony formed after plating was inoculated into 200 ml of LB solid medium and cultured until $OD_{600\ nm}$ became 0.4 at 30° C. L-arabinose was added at a concentration of 1 mM and further cultured for 3 hours to overexpress the lambda-red beta protein and Cpf1 protein. After centrifugation at 3500 rpm for 20 minutes, washing with 40 ml of 10% glycerol was performed twice to prepare electrocompetent cells. After electroporation, galactose was plated on a MacConkey plate selective medium with 5 g/L of galactose and cultured at 37° C.

When the crRNA plasmid is inserted into the HK1061 strain overexpressing the Cpf1 protein, the crRNA/Cpf1 complex is formed, and a double-stranded break occurs in the target DNA sequence complementary to the crRNA. When a double-stranded break occurs, *E. coli* is killed because it does not have a system to repair the break. The reduction in CFU resulting from cell death may determine whether the CRISPR/Cpf1 gene scissors work.

When a mutation is introduced into the target DNA sequence of the gene scissors by oligonucleotide, the sequence into which the mutation is introduced is not recognized as the target DNA by the gene scissors so that cells may survive. On the other hand, non-mutagenic target DNA is recognized by gene scissors, and the double-stranded DNA is cleaved, resulting in cell death. This is called negative selection. Through negative selection, the target genome may be effectively edited and selected at the level of a single base.

The present inventors produced a stop codon at bases 503 to 505 in the galK gene of *E. coli* (NCBI accession no. 945358) to induce immature synthesis termination of GalK protein. In the case of edited cells, white colonies were formed in McConkey's selective medium containing galactose, and unmutated cells formed red colonies. A system was constructed to estimate the editing efficiency by the ratio of each color of the colonies formed in McConkey's solid medium [white colony/(white colony+red colony)] (FIG. 1A), and the effect of editing 1 to 3 bases by negative selection was confirmed.

Figure 1B:
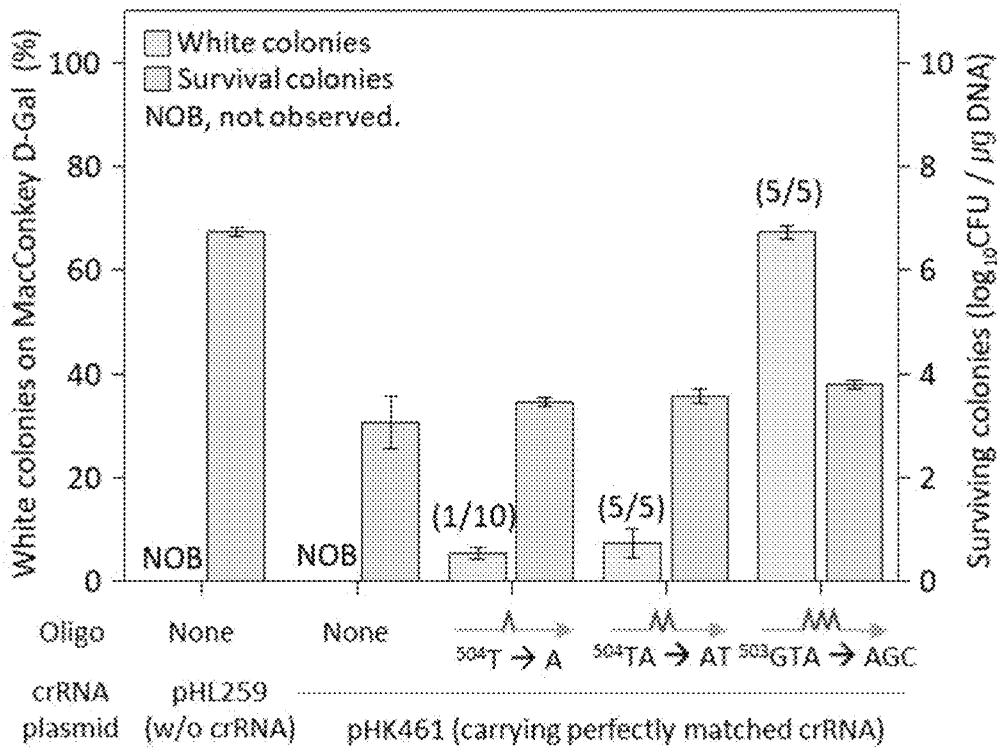
FIG. 1B shows the low efficiency of single and double base editing using oligonucleotide-induced mutation.

When a plasmid that does not express crRNA was inserted by electroporation, negative selection did not occur, resulting in a CFU level of $10^7$/μg DNA (FIG. 1B). As a result of inserting only a plasmid expressing crRNA without an oligonucleotide, it was shown that the CFU was reduced to the level of $10^3$/μg DNA by negative selection. It is considered that the crRNA/complex normally causes double-strand breaks in the target DNA, resulting in cell death. When the oligonucleotide and crRNA expression plasmid were inserted together, the single-base or double-base editing efficiency was low at 5% and 7% or less, respectively, whereas the editing efficiency of three bases was 67%, which was significantly higher than that of single and double base editing.

To check the accuracy of base editing, ten, five, and five colonies formed in white color in McConkey's selective medium were selected and sequenced for each number of base edits. As a result, as shown in FIG. 2, only one of the ten white colonies generated when a single base editing oligonucleotide was inserted correctly changed only the 504 target base, and unwanted additional mutations were observed in the remaining nine colonies. On the other hand, it was confirmed that only the targeted bases were accurately changed in all five colonies in the case of double and triple base editing. When the single base editing efficiency and sequence analysis results were combined, it was confirmed that only 0.5%, which is 1/10 of the 5% formed in McConkey's selective medium, was edited correctly, significantly reducing editing efficiency and accuracy.

Figure 1C:
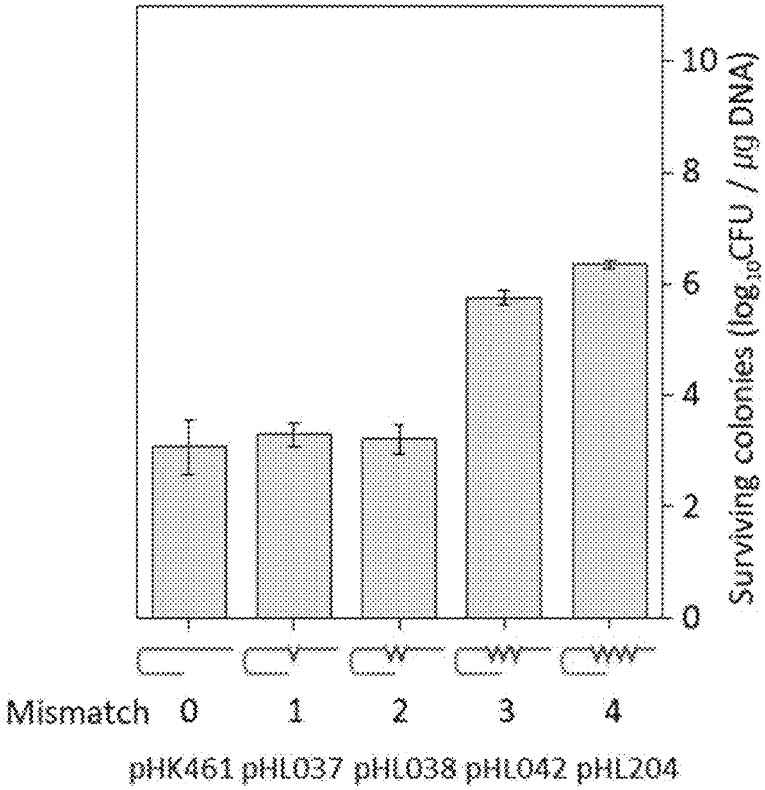
FIG. 1C shows the mismatch-tolerant properties of CRISPR/Cpfl.

Additionally, in order to confirm the mismatch tolerance of CRISPR/Cpf1, negative selection was performed with a mismatch plasmid in which 1 to 4 mismatched bases and a mismatch were assigned to the crRNA complementary to the target DNA. As a result, it was shown that when there are two or less mismatched bases in the crRNA, the CFU was $10^3$/μg DNA level due to negative selection, but when there are 3 or more mismatches in the crRNA, the target was not recognized, and negative selection was not performed so that CFU was significantly increased to $10^6$/μDNA or more (FIG. 1C). The results demonstrate the properties of Cpf1 to cause mismatch tolerance between the target DNA and the complementary crRNA, and the difficulty of editing single or double bases.

Example 2. 3'-end Truncation of CRISPR/Cpf1 crRNA and Single Base Mismatch Intolerance Previous studies reported that the crRNA/Cpf1 complex may cause double-strand breaks in the target DNA even when the 3' end of the CRISPR/Cpf1 crRNA is removed by 4 to 6 nucleotides (nt). The present inventors introduced a crRNA plasmid in which the 3'-end of the crRNA was removed by 1 to 6 nt into HK1061 cells to confirm the operation of the gene scissors so that they were intended to confirm the characteristics of the mismatch tolerance and truncation tolerance of CRISPR/Cpf1.

Figure 3A:
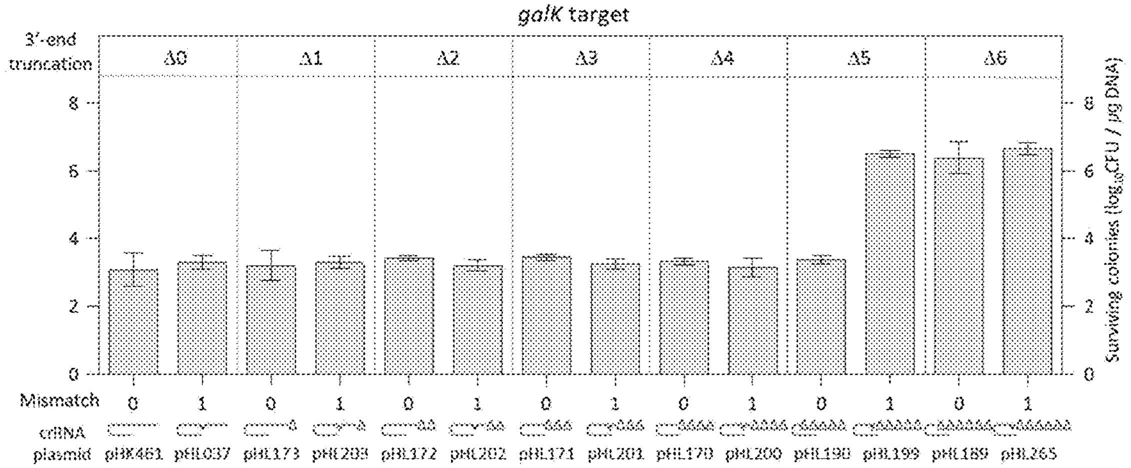
FIGS. 3A and 3B are graphs showing cleavage tolerance in galK(A) and xylB(B) genes using 3'-end truncated crRNA and the ability to discriminate single base mismatches at the maximum length of 3'-end cleavage, respectively.
Figure 3B:
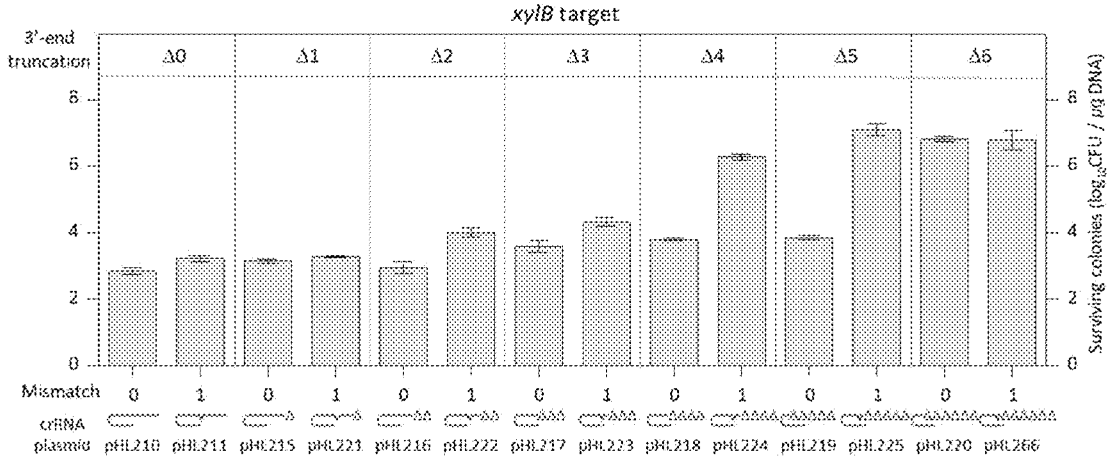

As a result, as shown in FIGS. 3A to 3B, it was confirmed that the CFU decreased to the level of $10^3$/μDNA even when the 3'-end of crRNA was cut by 5 nt. However, when the 3'-end truncation was present for 6 nt or more in crRNA, the CFU was elevated to the level of $10^7$/μDNA, probably because the 3'-end 6 nt-truncated crRNA/Cpf1 complex gene scissors did not work. Additionally, 1 to 6 3'-end truncation and single base mismatches were simultaneously given to the crRNA, and it was observed that the 3'-end 6 nt-truncated crRNA did not have mismatch tolerance and could be distinguished from a single mismatch with the target. In the case of crRNA having a single mismatch up to the truncation of 4 nt or less at the 3' end at the same time, CFU was reduced by negative selection. On the other hand, when a single mismatch and a 3' 5-nt truncation were simultaneously present, the CFU was significantly elevated at $10^{6-7}$/μg DNA level compared to that only the presence of 3' 5-nt truncation in crRNA could cause double-stranded break in cells.

Figure 3C:
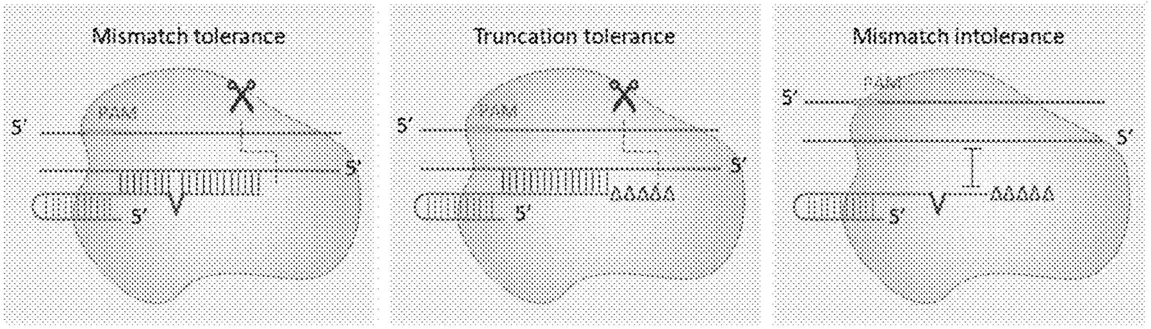
FIG. 3C shows a conceptual diagram of the same.

Accordingly, the present inventors applied 3'-end truncated crRNA to a single base editing method based on the result that it was not recognized as a target when both 3' 5 nt-truncation and a single mismatch exist in crRNA in CRISPR/Cpf1 (FIG. 3C).

TABLE 1

| SEQ ID NO | Primer Name | Primer sequence (5'→3') |
|---|---|---|
| 1 | P1 | CAATAACTAAGTCCCTTTGAGTGAGCTGATACCGCTCGCCG |
| 2 | P2 | CAAGAACCAGGACCGGTAATACGGTTATCCACAGAATCAGG |
| 3 | P3 | AACCGTATTACCGGTCCTGGTTCTTGTCCTGGGCAACGTTG |
| 4 | P4 | GATTCCGCGAACCCCAGAGTCCCGCAGGAGCCTCAAAAATCGAGCTCG CTTTGGTC |
| 5 | P5 | CAAAGCGAGCTCGATTTTTGAGGCTCCTGCGGGACTCTGGGGTTCGCG GAATCATG |
| 6 | P6 | GCTCACTCAAAGGGACTTAGTTATTGCGGTTCTGGACAAAT |
| 7 | galK504A | GAAAACCAGTTTGTAGGCTGAAACTGCGGGATCATGGATCA |
| 8 | galK504_del | GAAAACCAGTTTGTAGGCTGAACTGCGGGATCATGGATCA |
| 9 | galK504_insC | GAAAACCAGTTTGTAGGCTGCTAACTGCGGGATCATGGATCA |
| 10 | galK510_del | CAGTTTGTAGGCTGTAACTGGGGATCATGGATCAGCTAAT |
| 11 | galK510_insG | CAGTTTGTAGGCTGTAACTGGCGGGATCATGGATCAGCTAAT |
| 12 | galK505C_F | TAGGCTGTCACTGCGGGATCAATTTAAATAAAACGAAAGGCTCAGTC |
| 13 | galK505C_R | TGATCCCGCAGTGACAGCCTAATCTACAACAGTAGAAATTCGGATCC |
| 14 | galK505GG_F | TAGGCTGTGGCTGCGGGATCAATTTAAATAAAACGAAAGGCTCAGTC |
| 15 | galK505GG_R | TGATCCCGCAGCCACAGCCTAATCTACAACAGTAGAAATTCGGATCC |
| 16 | galK505CCA_F | TAGGCTGTCCATGCGGGATCAATTTAAATAAAACGAAAGGCTCAGTC |
| 17 | galK505CCA_R | TGATCCCGCATGGACAGCCTAATCTACAACAGTAGAAATTCGGATCC |
| 18 | galK_15_F | GTAGATTAGGCTGTAACTGCGATTTAAATAAAACGAAAGGCTCAGTC |
| 19 | galK_15_R | CGCAGTTACAGCCTAATCTACAACAGTAGAAATTCGGATCC |

TABLE 1-continued

| SEQ ID NO | Primer Name | Primer sequence (5'→3') |
|---|---|---|
| 20 | galK_16_F | TAGATTAGGCTGTAACTGCGGATTTAAATAAAACGAAAGGCTCAGTC |
| 21 | galK_16_R | CCGCAGTTACAGCCTAATCTACAACAGTAGAAATTCGGATCC |
| 22 | galK_17_F | AGATTAGGCTGTAACTGCGGGATTTAAATAAAACGAAAGGCTCAGTC |
| 23 | galK_17_R | CCCGCAGTTACAGCCTAATCTACAACAGTAGAAATTCGGATCC |
| 24 | galK_18_F | GATTAGGCTGTAACTGCGGGAATTTAAATAAAACGAAAGGCTCAGTC |
| 25 | galK_18_R | TCCCGCAGTTACAGCCTAATCTACAACAGTAGAAATTCGGATCC |
| 26 | galK_19_F | ATTAGGCTGTAACTGCGGGATATTTAAATAAAACGAAAGGCTCAGTC |
| 27 | galK_19_R | ATCCCGCAGTTACAGCCTAATCTACAACAGTAGAAATTCGGATCC |
| 28 | galK_20_F | TTAGGCTGTAACTGCGGGATCATTTAAATAAAACGAAAGGCTCAGTC |
| 29 | galK_20_R | GATCCCGCAGTTACAGCCTAATCTACAACAGTAGAAATTCGGATCC |
| 30 | galK505CCAG_21_F | TAGGCTGTCCAGGCGGGATCAATTTAAATAAAACGAAAGGCTCAGTC |
| 31 | galK505CCAG_21_R | TGATCCCGCCTGGACAGCCTAATCTACAACAGTAGAAATTCGGATCC |
| 32 | galK505C_20_F | TTAGGCTGTCACTGCGGGATCATTTAAATAAAACGAAAGGCTCAGTC |
| 33 | galK505C_20_R | GATCCCGCAGTGACAGCCTAATCTACAACAGTAGAAATTCGGATCC |
| 34 | galK505C_19_F | ATTAGGCTGTCACTGCGGGATATTTAAATAAAACGAAAGGCTCAGTC |
| 35 | galK505C_19_R | ATCCCGCAGTGACAGCCTAATCTACAACAGTAGAAATTCGGATCC |
| 36 | galK505C_18_F | GATTAGGCTGTCACTGCGGGAATTTAAATAAAACGAAAGGCTCAGTC |
| 37 | galK505C_18_R | TCCCGCAGTGACAGCCTAATCTACAACAGTAGAAATTCGGATCC |
| 38 | galK505C_17_F | AGATTAGGCTGTCACTGCGGGATTTAAATAAAACGAAAGGCTCAGTC |

TABLE 1-continued

| SEQ ID NO | Primer Name | Primer sequence (5'→3') |
|---|---|---|
| 39 | galK505C_17_R | CCCGCAGTGACAGCCTAATC TACAACAGTAGAAATTCGGA TCC |
| 40 | galK505C_16_F | TAGATTAGGCTGTCACTGCG GATTTAAATAAAACGAAAGG CTCAGTC |
| 41 | galK505C_16_R | CCGCAGTGACAGCCTAATCT ACAACAGTAGAAATTCGGAT CC |

Example 3. Single Base Editing using 3'-end Truncated crRNA

Figure 4A:
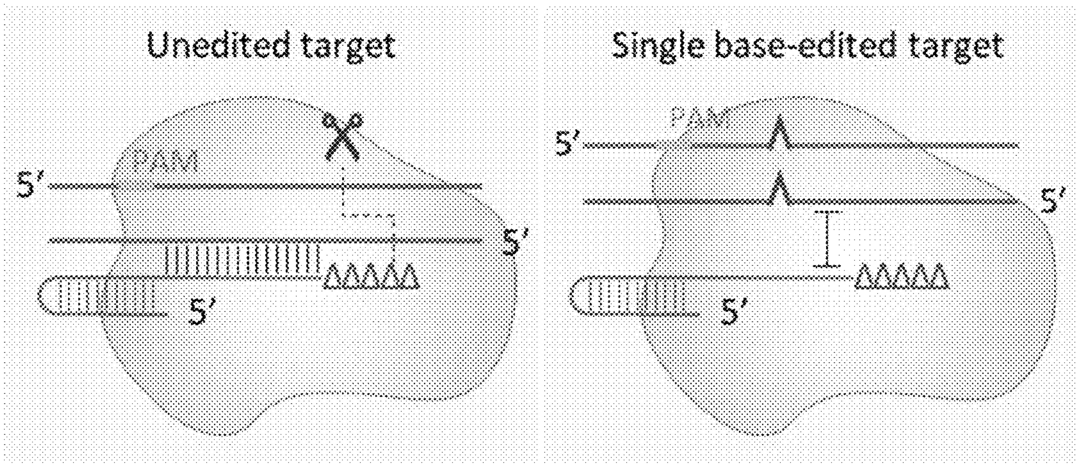
FIG. 4A shows a conceptual diagram applied to single base editing based on FIG. 3, and FIG. 4B and 4C are graphs showing the improvement of single base editing ability of the actual 3'-end truncated crRNA.

Based on the results of Example 2, the present inventors attempted to increase single base editing efficiency by applying to base editing that a single base mismatch is distinguished when the 3'-end truncation is maximally present (FIG. 4A). Mutagenic oligonucleotides were prepared so that one base each of 504 of the galK gene and 643 of the xylB (NCBI accession no. 948133) gene were substituted. The single base editing efficiency of CRISPR/Cpf1 using a 3'-end truncated crRNA was calculated with a ratio by a color of colonies formed in McConkey solid medium after a crRNA expression plasmid and a mutagenic oligonucleotide were electroporated into HK1061 in the same manner as in Example 1.

Figure 4B:
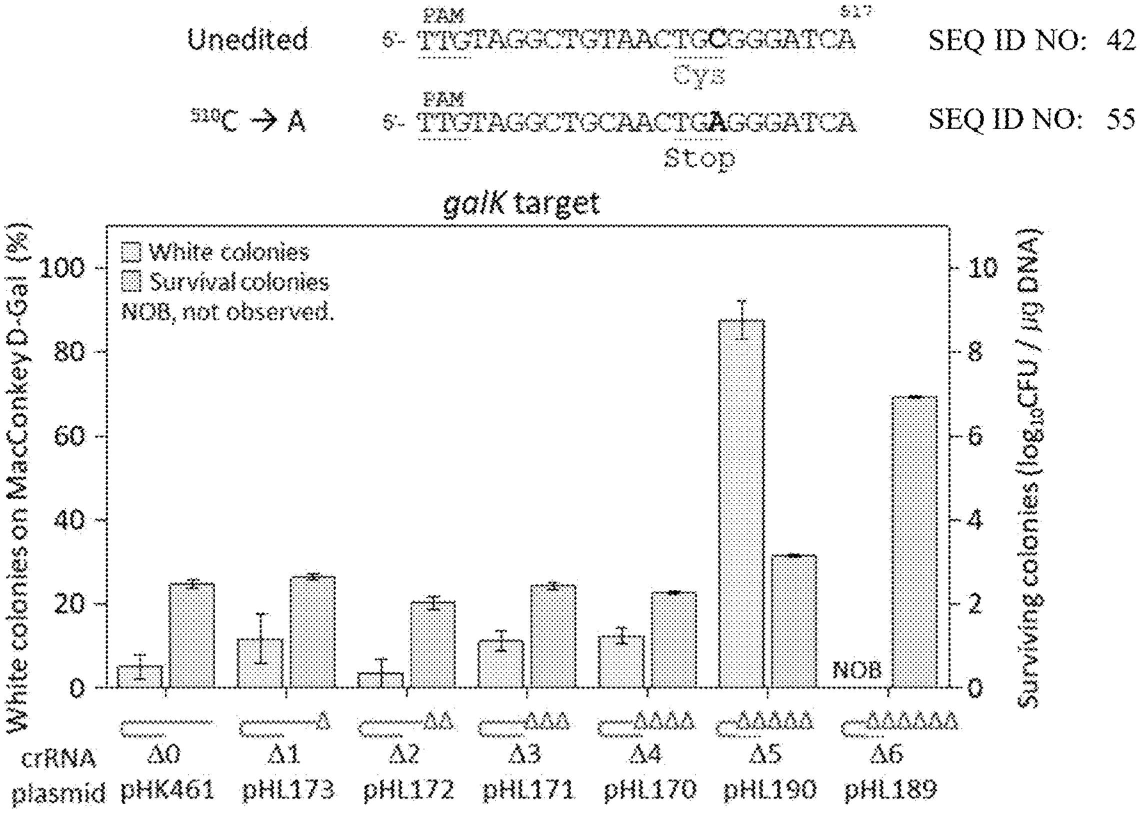
Figure 4C:
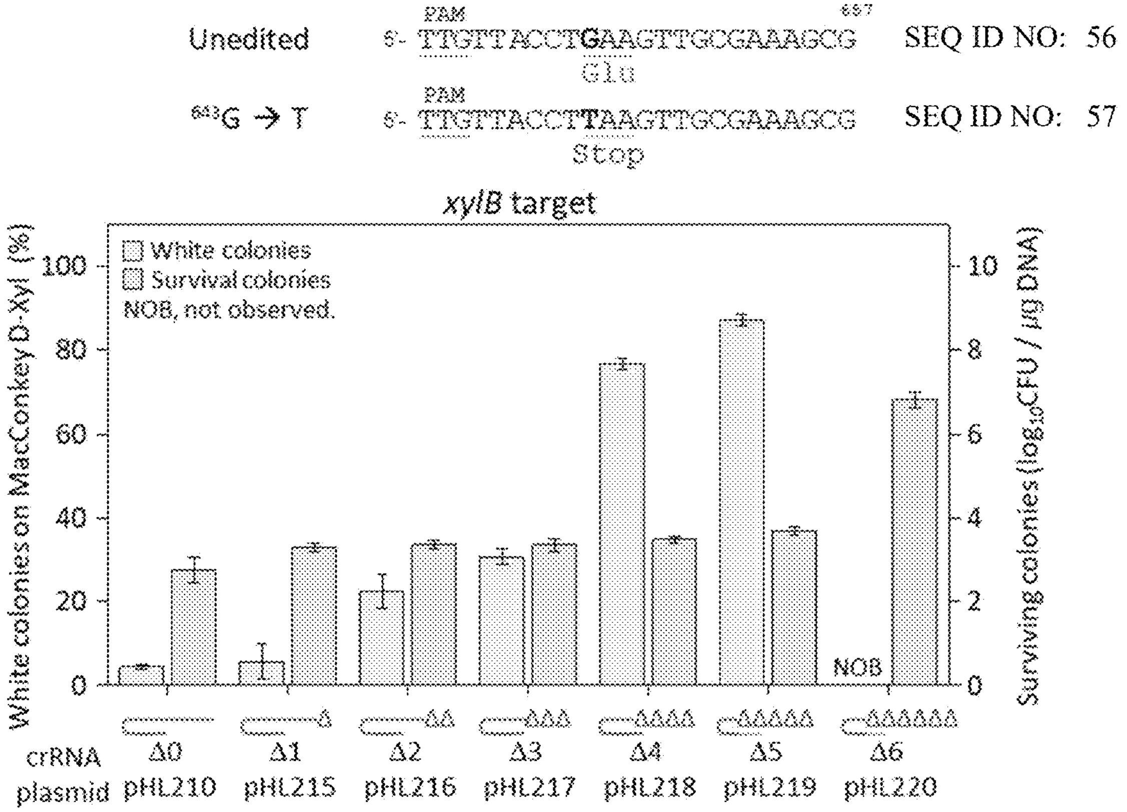
Figure 5:
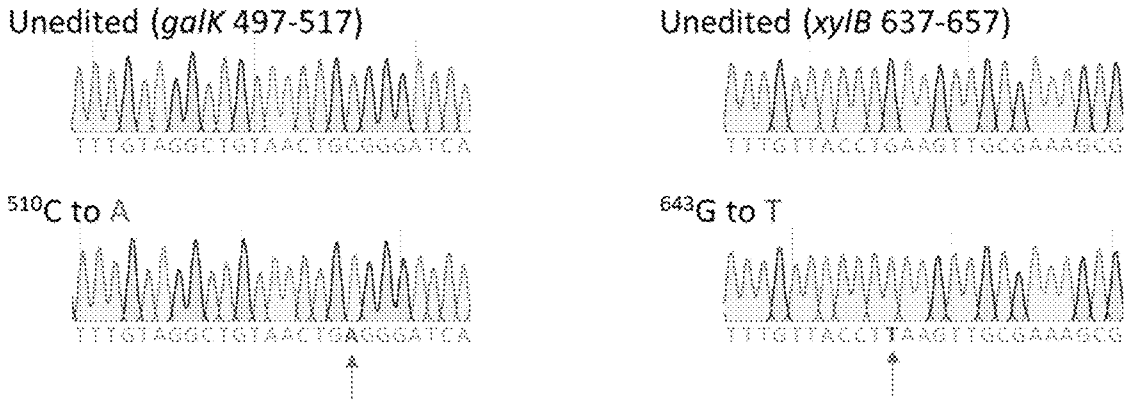
FIG. 5 shows a Sanger sequence analysis result of the single base editing target site of FIG. 4, indicating the accuracy of single base editing of the 3'-end truncated crRNA. The sequences shown in the figure are identified as follows.

In single base editing of the galK gene, when there was a truncation of 4 nt or less at the 3'-end of the crRNA, less than 10% of white colonies were formed due to the mismatch/truncation tolerance of the CRISPR/Cpf1 system (FIG. 4B). In the xylB gene, as the number of 3'-end truncation of crRNA increased from 0 to 4 nt, the percentage of white colonies gradually increased from 4% to 76% (FIG. 4C). In both genes, when a 5 nt truncation was present at the 3'-end of crRNA, both galK 504 base and xylB 643 base showed a significant increase in the proportion of white colonies generated by single base editing to 87%. Thereafter, the sequence analysis confirmed that only base 504 of the galK gene and base 643 of the xylB gene were correctly changed (FIG. 5).

These results show that the presence of a 5 nt truncation at the 3'-end of the crRNA of CRISPR/Cpf1 induces a double-strand break in the unmutated target, but a target having a single base mismatch due to mutation is not recognized as a target to obtain a single base edited strain.

Figure 6A:
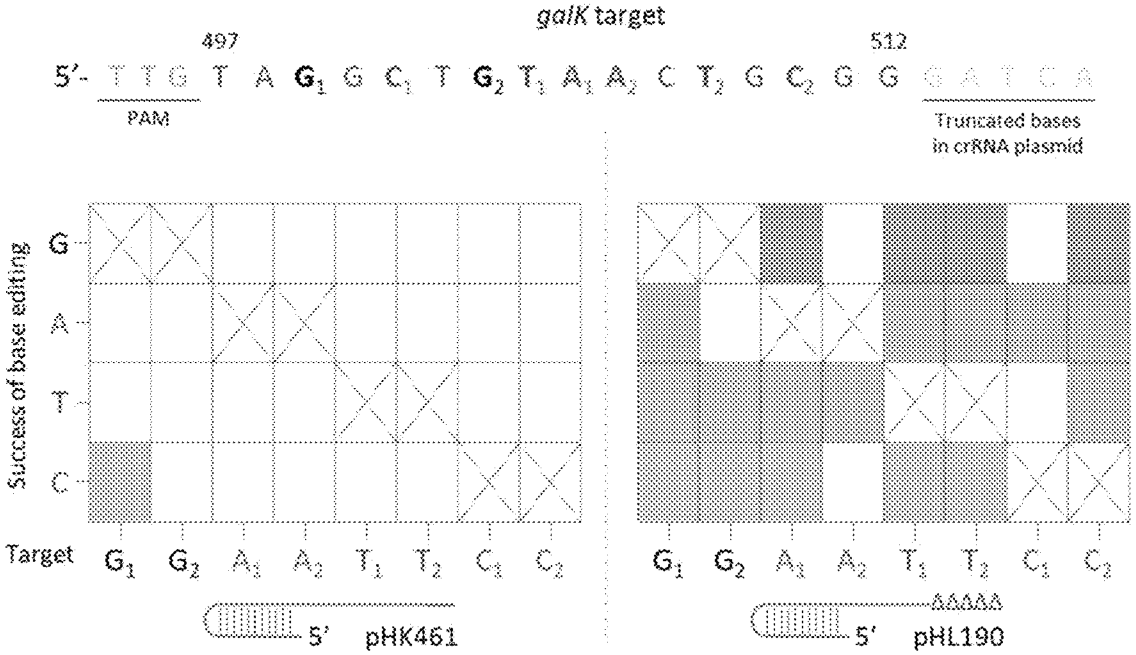
FIGS. 6A and 6B are tables showing actual base editing results through sequence analysis of randomly selected galK(A) and xylB(B) targets, respectively, after single base editing.
Figure 6B:
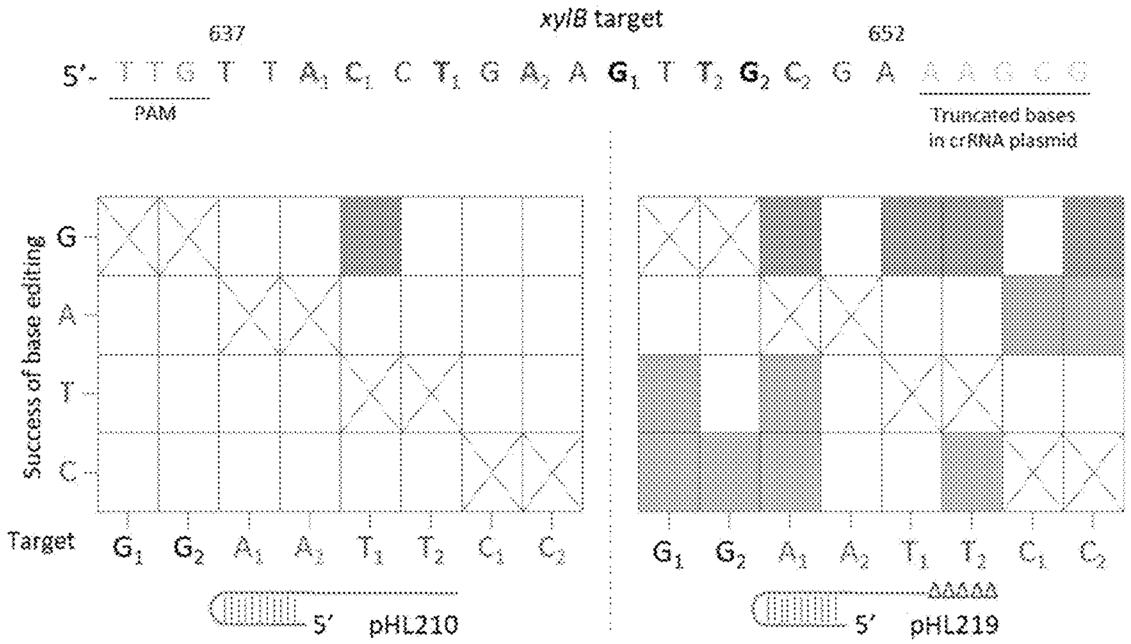
Figure 7:
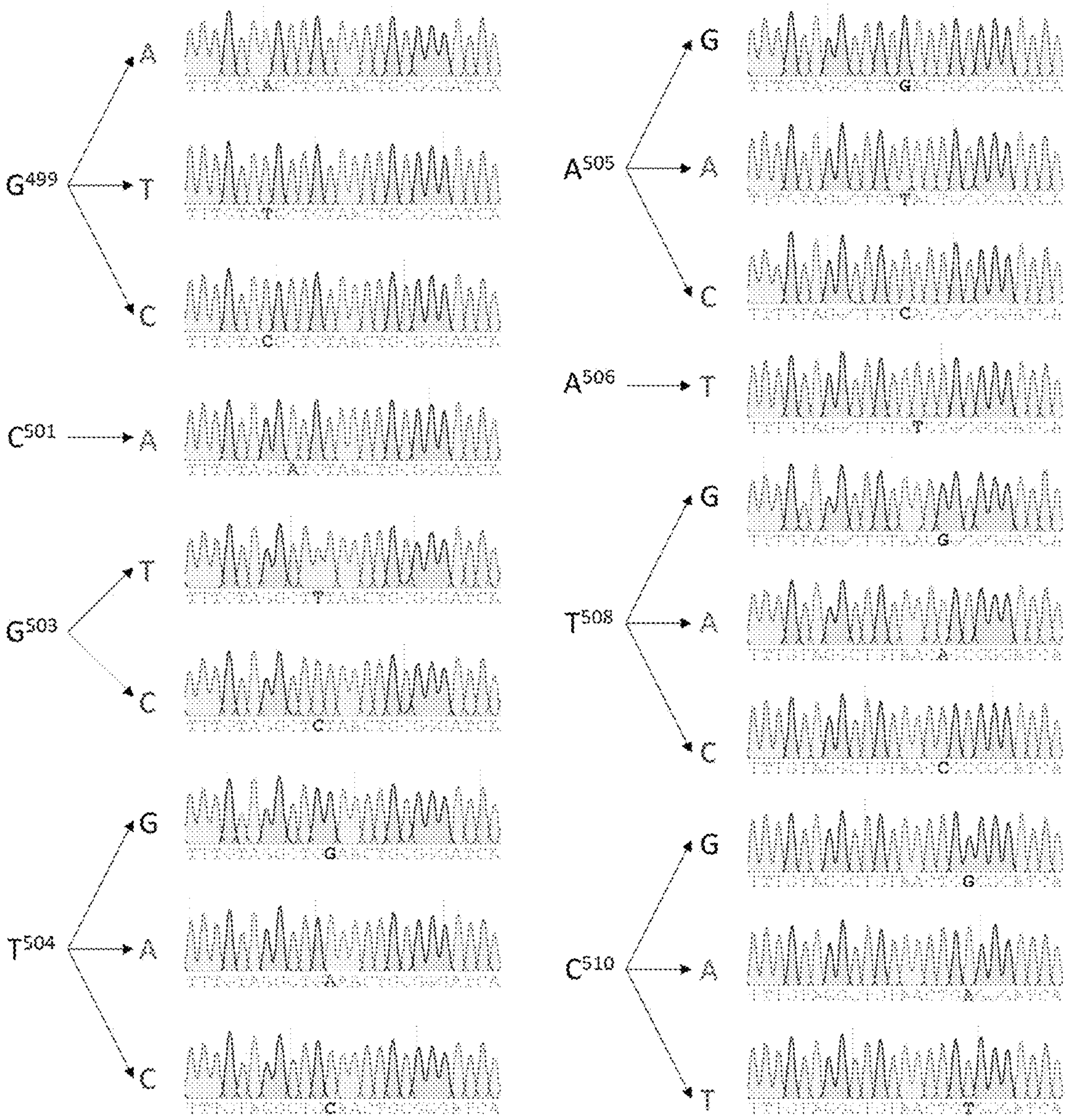
FIG. 7 shows the nucleotide sequence analysis results of randomly selected galK targets after single base editing performed in FIG. 6A. The sequences shown in the figure are identified as follows.
Figure 8:
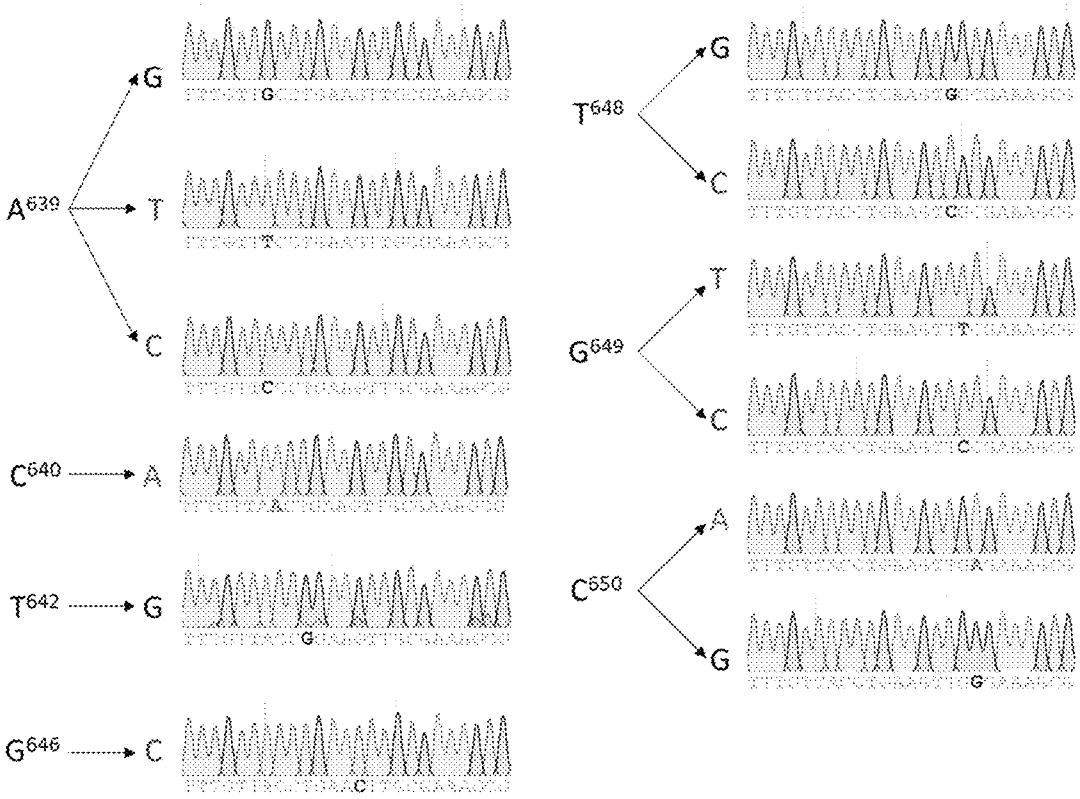
FIG. 8 shows the nucleotide sequence analysis results of xylB targets randomly selected after single base editing performed in FIG. 6B. The sequences shown in the figure are identified as follows.

Example 4. Verification of Single Base Editing Efficiency of 3'-end Truncated crRNA Through Random Candidate Sequencing The present inventors tried to confirm whether the ability of the 3'-end truncated crRNA to improve the single base editing efficiency may be applied to various targets other than 504 of galK, and 643 of xylB. In order to perform all possible edits at the base at various positions within the same target DNA sequence $N_{21}$, an oligonucleotide was constructed to substitute three different bases except for itself (A→G/T/C, T→G/A/C, G→A/T/C, or C→G/A/T). A total of 8 target bases for each gene were set as two each for G, A, T, and C. Three single base editing oligonucleotides were constructed per position of one target base. Thus, a total of 24 electroporations (=possible base editing) were performed (FIGS. 6A to 6B). Four colonies were randomly selected from the colonies formed after plating on LB medium supplemented with spectinomycin at 75 $\mu g ml^{-1}$. Sanger sequencing confirmed the single base editing ability in which when a single base was correctly changed in even one colony, it was considered as a success (FIGS. 7 to 8).

Figure 6C:
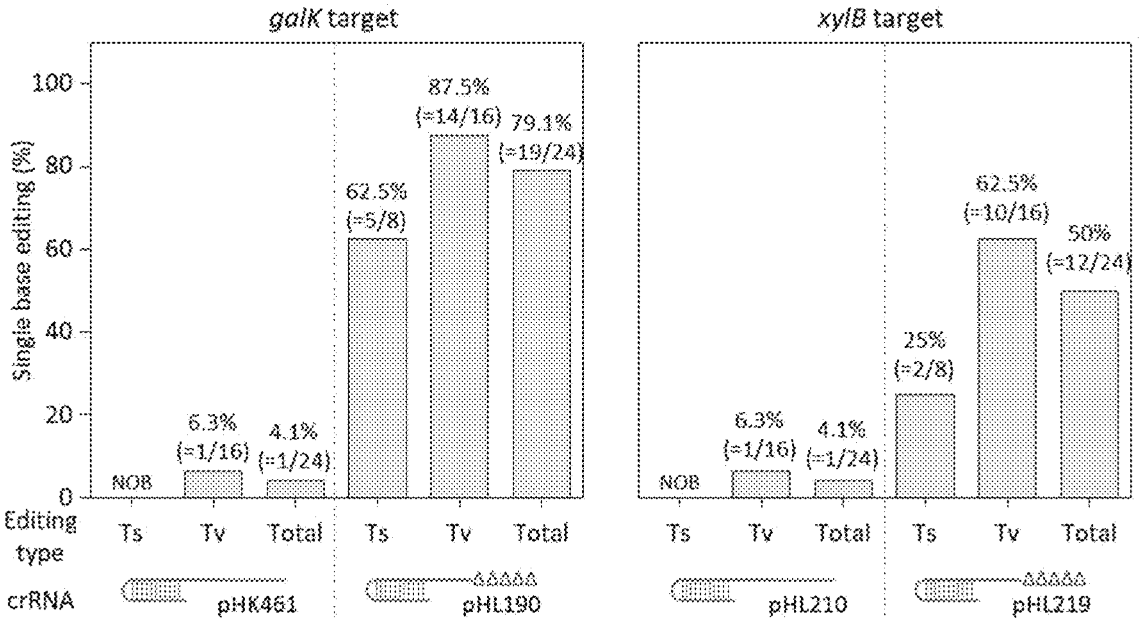
FIG. 6C is a graph showing the success rate according to the type of mutation, respectively. The sequences shown in the figures are identified as follows.

In order to compare the improvement in single base editing efficiency of 3'-end truncated crRNA, the base editing ability was first confirmed with a crRNA plasmid without 3'-end truncation. The results indicate that only one of 24 base edits was successful in both galK and xylB genes (FIGS. 6A to 6B). On the other hand, when the 3'-end 5 nt truncated crRNA showing the maximum editing efficiency in each gene was used, 79.1% of the galK gene (19 of 24 edited) and 50% of the xylB gene (12 of 24) were shown so that the single base editing ability was significantly improved in both genes. The results of 19 edits of galK and 12 edits of xylB (/24 edits), which were successful in introducing mutations, were analyzed by mutation type (8 transition+16 transversion). In galK, the transition was 62.5% (=5/8) and transversion was 87.5% (=14/16), respectively. In xylB, transition was 25% (=2/8) and transversion was 62.5% (=10/16), respectively. These results indicate that transversion was more predominant in both genes (FIG. 6C). This demonstrates that the 3'-end truncated crRNA of the present disclosure is an optimal condition in which single base editing ability is greatly improved at the maximum number of truncations, and it shows that transversion-type base editing may be performed better.

Example 5. Confirmation of Single Nucleotide Insertion/Deletion Editing Efficiency of 3'-end Truncated crRNA The present inventors confirmed whether the 3'-end truncated crRNA affects not only single base editing but also the improvement of single nucleotide insertion or deletion efficiency.

The brief is as follows.

When base 509 of the galK gene is deleted, or a single nucleotide is inserted at position 510, a frame shift of the galK gene occurs to generate a stop codon at base 600's, leading to premature translation termination so that the GalK protein is not synthesized normally. Strains with single nucleotide deletion or insertion may not normally metabolize galactose and form white colonies on the McConkey medium. Therefore, it is possible to estimate the efficiency of deletion or insertion of a single nucleotide by checking change in the color of colonies formed in McConkey's medium. In the same principle, a mutation-inducing oligonucleotide was prepared so that base 643 in xylB was deleted or inserted. It was inserted into HK1061 together with crRNA plasmids having 0, 4, 5, and 6 nt truncation at 3' of crRNA, and the color change of colonies formed in McConkey's medium was observed.

Figure 9A:
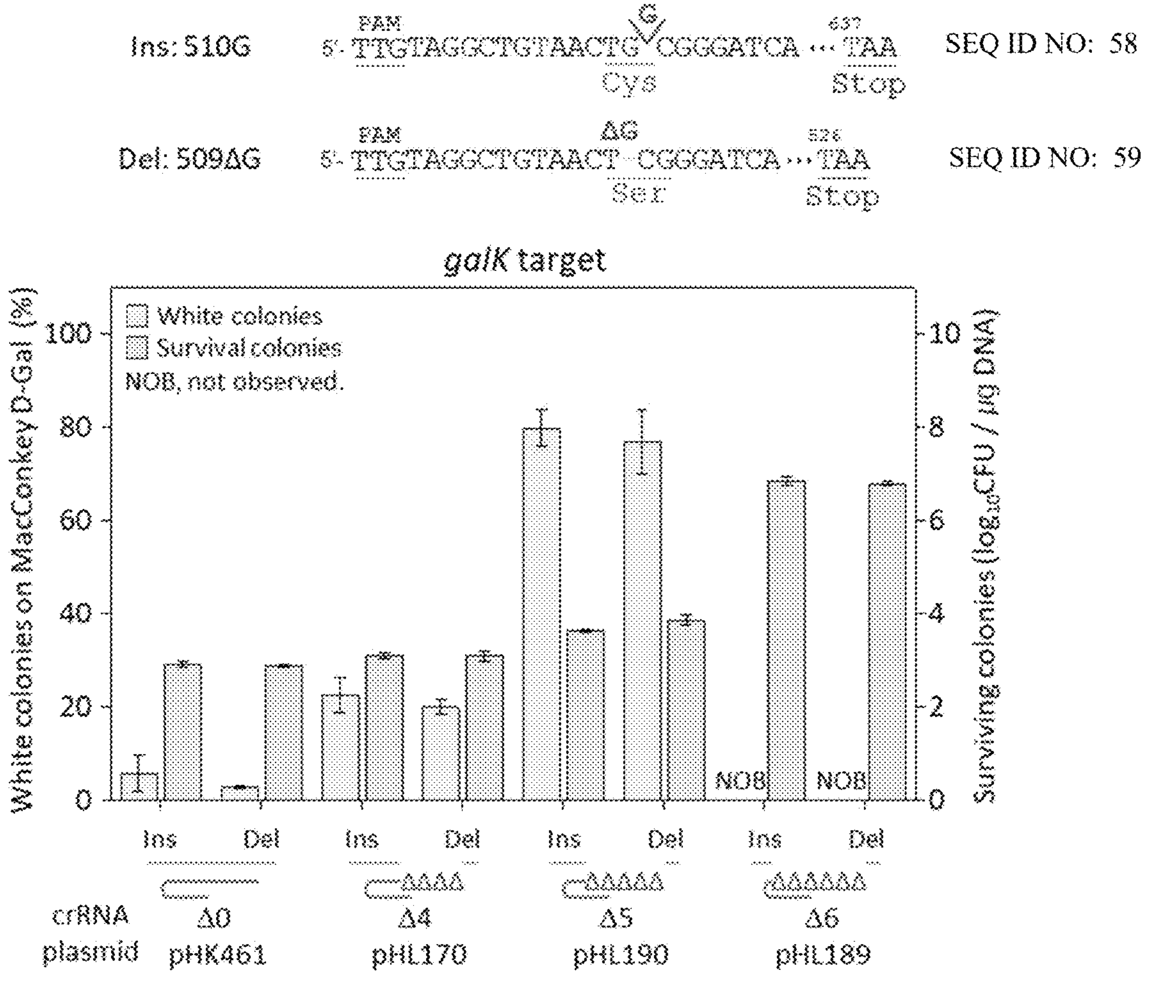
FIGS. 9A and 9B are graphs showing the results of single nucleotide insertion/deletion editing of galK(A) and xylB (B) genes using 3'-end truncated crRNA.
Figure 9B:
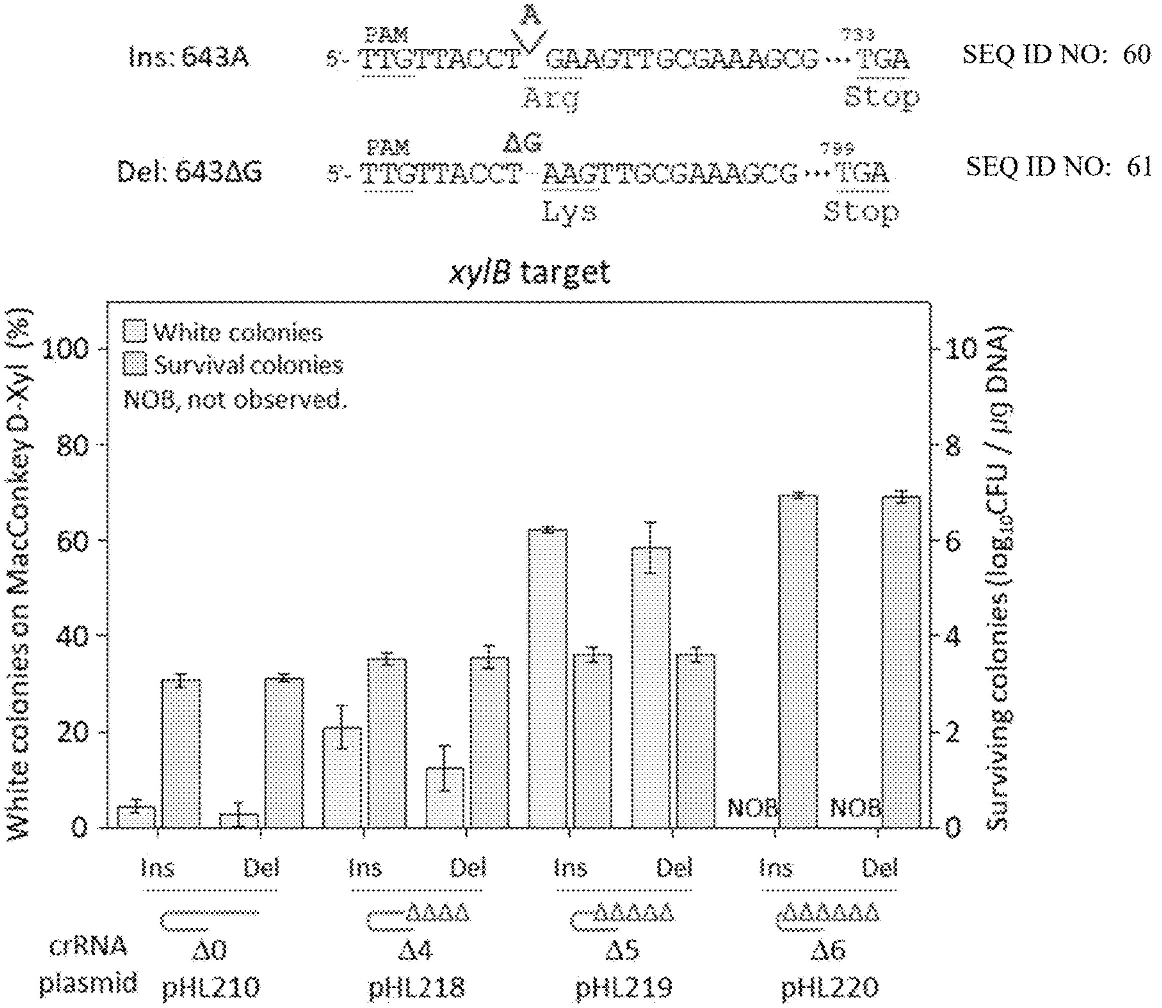

As a result, in the case of using an untruncated crRNA plasmid, single nucleotide insertion/deletion editing efficiency showed less than 10% in both galK and xylB genes. In the case of the 3'-end 4 nt truncated crRNA plasmid, the single nucleotide insertion efficiency at base 510 of galK was 22%, and the single nucleotide deletion efficiency at base 509 of galK was 19% (FIG. 9A). The insertion efficiency at base 643 of the xylB gene was slightly increased to 20%, and the single nucleotide deletion efficiency at base 643 was slightly increased to 12%.

Figure 10:
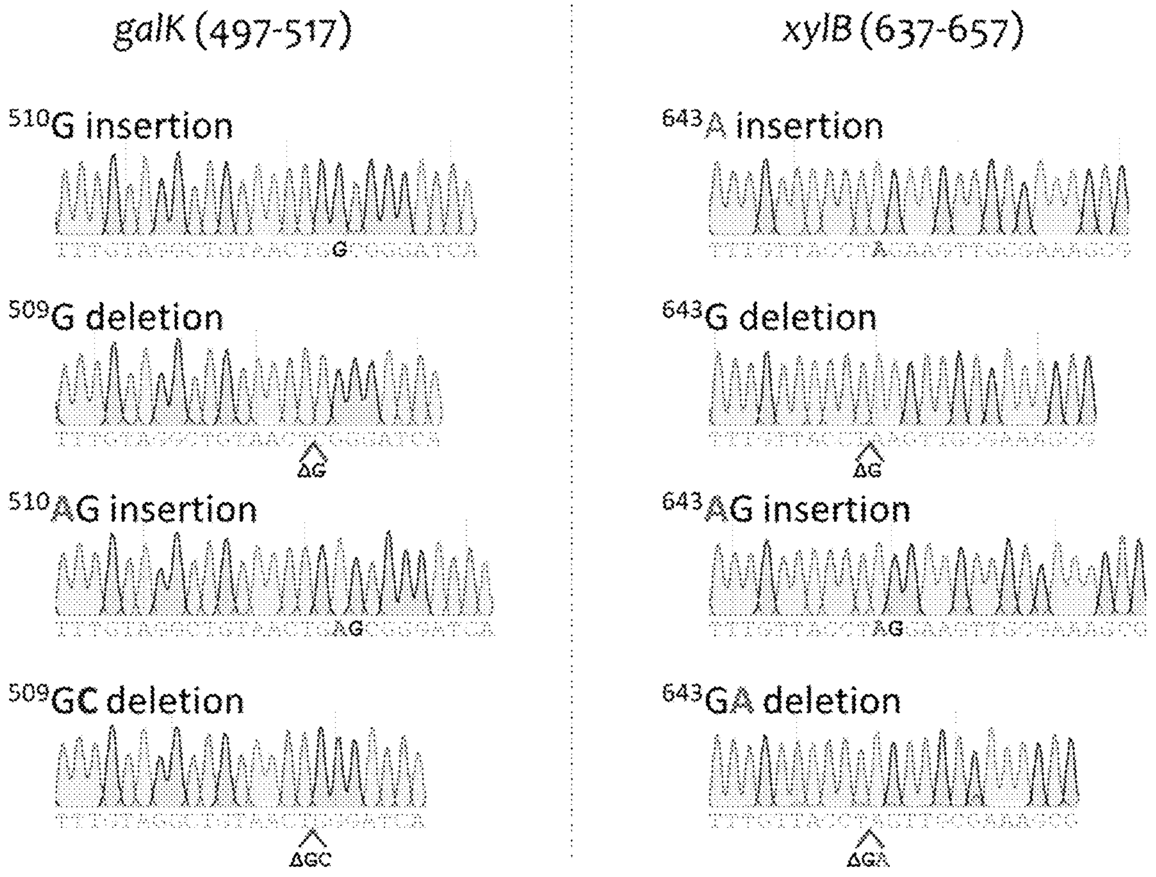
FIG. 10 shows a nucleotide sequence analysis result of a target site after single nucleotide insertion/deletion editing in FIG. 9. The sequences shown in the figure are identified as follows.

Meanwhile, in the case of the 3'-end 5 nt truncated crRNA plasmid, the single nucleotide insertion efficiency at base 510 of galK was significantly increased to 79%, and the nucleotide deletion efficiency at base 509 was significantly increased to 76%. The insertion efficiency of the xylB gene at base 643 was significantly increased to 62%, and the single nucleotide deletion efficiency at base 643 was significantly increased to 58%. The nucleotide sequence analysis confirmed that only the target base was accurately changed (FIG. 10). When the 3'-end 6 nt truncated crRNA plasmid was used, the CFU was elevated to the level of $10^7$/μg DNA, regardless of the nucleotide deletion or insertion site. These results show the same trend as in Example 1. These results show that it is most effective for all types of genome editing, including single base editing, insertion, or deletion within the maximum length where the 3'-end truncation of Cpf1 crRNA is allowed.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. A method for single-base genome editing based on a CRISPR/Cpf1 system comprising crRNA (CRISPR RNA) and a donor nucleic acid molecule that complementarily binds to a target DNA, the method comprising (a) generating one mismatched nucleotide between the target DNA and the crRNA sequence by the donor nucleic acid molecule; (b) truncating nucleotides from the 3'-end of crRNA, thereby the 3'-end-truncated crRNA comprises a region consisting of 15 to 20 consecutive nucleotides complementary to the target DNA; and (c) contacting the CRISPR/Cpf1 system with the target DNA of a genome, and wherein the 5-nt 3'-end-truncated crRNA has one nucleotide mismatch with the target DNA into which a point mutation is induced by the donor nucleic acid molecule, wherein the 5-nt 3'-end-truncated crRNA loses mismatch tolerance when combined with the one mismatched nucleotide, and wherein the donor nucleic acid is a separate nucleic acid in single-stranded form from the crRNA.

2. The method of claim 1, wherein the target DNA comprises a nucleotide of a sequence complementary to the crRNA and a protospacer-adjacent motif (PAM).

3. The method of claim 1, wherein the donor nucleic acid molecule induces the point mutation that is a single-base substitution, insertion, or deletion in the target DNA.

4. A method for increasing genome editing efficiency based on a CRISPR/Cpf1 system comprising crRNA (CRISPR RNA) and a donor nucleic acid molecule that complementarily binds to a target DNA, the method comprising generating one mismatched nucleotide between the target DNA and the crRNA sequence by the donor nucleic acid molecule; truncating nucleotides from the 3'-end of crRNA, thereby the 3'-end-truncated crRNA comprises a region consisting of 15 to 20 consecutive nucleotides complementary to the target DNA; and contacting the CRISPR/Cpf1 system with the target DNA of a genome, and wherein the 5-nt 3'-end-truncated crRNA has one nucleotide mismatch with the target DNA into which a point mutation is induced by the donor nucleic acid molecule, wherein the 5-nt 3'-end-truncated crRNA loses mismatch tolerance when combined with the one mismatched nucleotide, and wherein the donor nucleic acid is a separate nucleic acid in single-stranded form from the crRNA.

5. A method for preparing a subject in which a target DNA is edited based on the CRISPR/Cpf1 system, comprising the steps of:

(a) constructing a donor nucleic acid molecule that complementarily binds to the target DNA and induces one mismatched nucleotide between the target DNA and crRNA sequence;

(b) constructing a 3'-truncated crRNA by truncating nucleotides from the 3'-end of crRNA, thereby the 3'-end-truncated crRNA comprises a region consisting of 15 to 20 consecutive nucleotides complementary to the target DNA; and (c) contacting the donor nucleic acid molecule of step (a) and the 3'-truncated crRNA of step (b) into the subject to be edited, thereby editing the target DNA of the subject, and wherein the 5-nt 3'-end-truncated crRNA has one nucleotide mismatch with the target DNA into which a point mutation is induced by the donor nucleic acid molecule, wherein the 5-nt 3'-end-truncated crRNA loses mismatch tolerance when combined with the one mismatched nucleotide, and wherein the donor nucleic acid is a separate nucleic acid in single-stranded form from the crRNA.

* * * * *

```
SEQUENCE LISTING

<160> NUMBER OF SEQ ID NOS: 86

<210> SEQ ID NO 1
<211> LENGTH: 41
<212> TYPE: DNA
<213> ORGANISM: Artificial Sequence
<220> FEATURE:
<223> OTHER INFORMATION: P1

<400> SEQUENCE: 1

caataactaa gtccctttga gtgagctgat accgctcgcc g                          41


<210> SEQ ID NO 2
<211> LENGTH: 41
<212> TYPE: DNA
<213> ORGANISM: Artificial Sequence
<220> FEATURE:
<223> OTHER INFORMATION: P2

<400> SEQUENCE: 2

caagaaccag gaccggtaat acggttatcc acagaatcag g                          41


<210> SEQ ID NO 3
<211> LENGTH: 41
<212> TYPE: DNA
<213> ORGANISM: Artificial Sequence
<220> FEATURE:
<223> OTHER INFORMATION: P3

<400> SEQUENCE: 3

aaccgtatta ccggtcctgg ttcttgtcct gggcaacgtt g                          41


<210> SEQ ID NO 4
<211> LENGTH: 56
<212> TYPE: DNA
<213> ORGANISM: Artificial Sequence
<220> FEATURE:
<223> OTHER INFORMATION: P4

<400> SEQUENCE: 4

gattccgcga accccagagt cccgcaggag cctcaaaaat cgagctcgct ttggtc          56


<210> SEQ ID NO 5
<211> LENGTH: 56
<212> TYPE: DNA
<213> ORGANISM: Artificial Sequence
<220> FEATURE:
<223> OTHER INFORMATION: P5

<400> SEQUENCE: 5

caaagcgagc tcgatttttg aggctcctgc gggactctgg ggttcgcgga atcatg          56
```

<210> SEQ ID NO 6
<211> LENGTH: 41
<212> TYPE: DNA
<213> ORGANISM: Artificial Sequence
<220> FEATURE:
<223> OTHER INFORMATION: P6

<400> SEQUENCE: 6
gctcactcaa agggacttag ttattgcggt tctggacaaa t 41

<210> SEQ ID NO 7
<211> LENGTH: 41
<212> TYPE: DNA
<213> ORGANISM: Artificial Sequence
<220> FEATURE:
<223> OTHER INFORMATION: galK504A

<400> SEQUENCE: 7
gaaaaccagt ttgtaggctg aaactgcggg atcatggatc a 41

<210> SEQ ID NO 8
<211> LENGTH: 40
<212> TYPE: DNA
<213> ORGANISM: Artificial Sequence
<220> FEATURE:
<223> OTHER INFORMATION: galK504_del

<400> SEQUENCE: 8
gaaaaccagt ttgtaggctg aactgcggga tcatggatca 40

<210> SEQ ID NO 9
<211> LENGTH: 42
<212> TYPE: DNA
<213> ORGANISM: Artificial Sequence
<220> FEATURE:
<223> OTHER INFORMATION: galK504_insC

<400> SEQUENCE: 9
gaaaaccagt ttgtaggctg ctaactgcgg gatcatggat ca 42

<210> SEQ ID NO 10
<211> LENGTH: 40
<212> TYPE: DNA
<213> ORGANISM: Artificial Sequence
<220> FEATURE:
<223> OTHER INFORMATION: galK510_del

<400> SEQUENCE: 10
cagtttgtag gctgtaactg gggatcatgg atcagctaat 40

<210> SEQ ID NO 11
<211> LENGTH: 42
<212> TYPE: DNA
<213> ORGANISM: Artificial Sequence
<220> FEATURE:
<223> OTHER INFORMATION: galK510_insG

<400> SEQUENCE: 11
cagtttgtag gctgtaactg gcgggatcat ggatcagcta at 42

<210> SEQ ID NO 12
<211> LENGTH: 47
<212> TYPE: DNA
<213> ORGANISM: Artificial Sequence
<220> FEATURE:
<223> OTHER INFORMATION: galK505C_F

<400> SEQUENCE: 12
taggctgtca ctgcgggatc aatttaaata aaacgaaagg ctcagtc 47

<210> SEQ ID NO 13
<211> LENGTH: 47
<212> TYPE: DNA
<213> ORGANISM: Artificial Sequence
<220> FEATURE:
<223> OTHER INFORMATION: galK505C_R

<400> SEQUENCE: 13
tgatcccgca gtgacagcct aatctacaac agtagaaatt cggatcc 47

<210> SEQ ID NO 14
<211> LENGTH: 47
<212> TYPE: DNA
<213> ORGANISM: Artificial Sequence
<220> FEATURE:
<223> OTHER INFORMATION: galK505GG_F

<400> SEQUENCE: 14
taggctgtgg ctgcgggatc aatttaaata aaacgaaagg ctcagtc 47

<210> SEQ ID NO 15
<211> LENGTH: 47
<212> TYPE: DNA
<213> ORGANISM: Artificial Sequence
<220> FEATURE:
<223> OTHER INFORMATION: galK505GG_R

<400> SEQUENCE: 15
tgatcccgca gccacagcct aatctacaac agtagaaatt cggatcc 47

<210> SEQ ID NO 16
<211> LENGTH: 47
<212> TYPE: DNA
<213> ORGANISM: Artificial Sequence
<220> FEATURE:
<223> OTHER INFORMATION: galK505CCA_F

<400> SEQUENCE: 16
taggctgtcc atgcgggatc aatttaaata aaacgaaagg ctcagtc 47

<210> SEQ ID NO 17
<211> LENGTH: 47
<212> TYPE: DNA
<213> ORGANISM: Artificial Sequence
<220> FEATURE:
<223> OTHER INFORMATION: galK505CCA_R

<400> SEQUENCE: 17
tgatcccgca tggacagcct aatctacaac agtagaaatt cggatcc 47

<210> SEQ ID NO 18
<211> LENGTH: 47
<212> TYPE: DNA
<213> ORGANISM: Artificial Sequence
<220> FEATURE:
<223> OTHER INFORMATION: galK_15_F

<400> SEQUENCE: 18
gtagattagg ctgtaactgc gatttaaata aaacgaaagg ctcagtc 47

<210> SEQ ID NO 19

<211> LENGTH: 41
<212> TYPE: DNA
<213> ORGANISM: Artificial Sequence
<220> FEATURE:
<223> OTHER INFORMATION: galK_15_R

<400> SEQUENCE: 19
cgcagttaca gcctaatcta caacagtaga aattcggatc c 41

<210> SEQ ID NO 20
<211> LENGTH: 47
<212> TYPE: DNA
<213> ORGANISM: Artificial Sequence
<220> FEATURE:
<223> OTHER INFORMATION: galK_16_F

<400> SEQUENCE: 20
tagattaggc tgtaactgcg gatttaaata aaacgaaagg ctcagtc 47

<210> SEQ ID NO 21
<211> LENGTH: 42
<212> TYPE: DNA
<213> ORGANISM: Artificial Sequence
<220> FEATURE:
<223> OTHER INFORMATION: galK_16_R

<400> SEQUENCE: 21
ccgcagttac agcctaatct acaacagtag aaattcggat cc 42

<210> SEQ ID NO 22
<211> LENGTH: 47
<212> TYPE: DNA
<213> ORGANISM: Artificial Sequence
<220> FEATURE:
<223> OTHER INFORMATION: galK_17_F

<400> SEQUENCE: 22
agattaggct gtaactgcgg gatttaaata aaacgaaagg ctcagtc 47

<210> SEQ ID NO 23
<211> LENGTH: 43
<212> TYPE: DNA
<213> ORGANISM: Artificial Sequence
<220> FEATURE:
<223> OTHER INFORMATION: galK_17_R

<400> SEQUENCE: 23
cccgcagtta cagcctaatc tacaacagta gaaattcgga tcc 43

<210> SEQ ID NO 24
<211> LENGTH: 47
<212> TYPE: DNA
<213> ORGANISM: Artificial Sequence
<220> FEATURE:
<223> OTHER INFORMATION: galK_18_F

<400> SEQUENCE: 24
gattaggctg taactgcggg aatttaaata aaacgaaagg ctcagtc 47

<210> SEQ ID NO 25
<211> LENGTH: 44
<212> TYPE: DNA
<213> ORGANISM: Artificial Sequence
<220> FEATURE:
<223> OTHER INFORMATION: galK_18_R

<400> SEQUENCE: 25
tcccgcagtt acagcctaat ctacaacagt agaaattcgg atcc 44

<210> SEQ ID NO 26
<211> LENGTH: 47
<212> TYPE: DNA
<213> ORGANISM: Artificial Sequence
<220> FEATURE:
<223> OTHER INFORMATION: galK_19_F

<400> SEQUENCE: 26
attaggctgt aactgcggga tatttaaata aaacgaaagg ctcagtc 47

<210> SEQ ID NO 27
<211> LENGTH: 45
<212> TYPE: DNA
<213> ORGANISM: Artificial Sequence
<220> FEATURE:
<223> OTHER INFORMATION: galK_19_R

<400> SEQUENCE: 27
atcccgcagt tacagcctaa tctacaacag tagaaattcg gatcc 45

<210> SEQ ID NO 28
<211> LENGTH: 47
<212> TYPE: DNA
<213> ORGANISM: Artificial Sequence
<220> FEATURE:
<223> OTHER INFORMATION: galK_20_F

<400> SEQUENCE: 28
ttaggctgta actgcgggat catttaaata aaacgaaagg ctcagtc 47

<210> SEQ ID NO 29
<211> LENGTH: 46
<212> TYPE: DNA
<213> ORGANISM: Artificial Sequence
<220> FEATURE:
<223> OTHER INFORMATION: galK_20_R

<400> SEQUENCE: 29
gatcccgcag ttacagccta atctacaaca gtagaaattc ggatcc 46

<210> SEQ ID NO 30
<211> LENGTH: 47
<212> TYPE: DNA
<213> ORGANISM: Artificial Sequence
<220> FEATURE:
<223> OTHER INFORMATION: galK505CCAG_21_F

<400> SEQUENCE: 30
taggctgtcc aggcgggatc aatttaaata aaacgaaagg ctcagtc 47

<210> SEQ ID NO 31
<211> LENGTH: 47
<212> TYPE: DNA
<213> ORGANISM: Artificial Sequence
<220> FEATURE:
<223> OTHER INFORMATION: galK505CCAG_21_R

<400> SEQUENCE: 31
tgatcccgcc tggacagcct aatctacaac agtagaaatt cggatcc 47

<210> SEQ ID NO 32
<211> LENGTH: 47
<212> TYPE: DNA

<213> ORGANISM: Artificial Sequence
<220> FEATURE:
<223> OTHER INFORMATION: galK505C_20_F

<400> SEQUENCE: 32
ttaggctgtc actgcgggat catttaaata aaacgaaagg ctcagtc 47

<210> SEQ ID NO 33
<211> LENGTH: 46
<212> TYPE: DNA
<213> ORGANISM: Artificial Sequence
<220> FEATURE:
<223> OTHER INFORMATION: galK505C_20_R

<400> SEQUENCE: 33
gatcccgcag tgacagccta atctacaaca gtagaaattc ggatcc 46

<210> SEQ ID NO 34
<211> LENGTH: 47
<212> TYPE: DNA
<213> ORGANISM: Artificial Sequence
<220> FEATURE:
<223> OTHER INFORMATION: galK505C_19_F

<400> SEQUENCE: 34
attaggctgt cactgcggga tatttaaata aaacgaaagg ctcagtc 47

<210> SEQ ID NO 35
<211> LENGTH: 45
<212> TYPE: DNA
<213> ORGANISM: Artificial Sequence
<220> FEATURE:
<223> OTHER INFORMATION: galK505C_19_R

<400> SEQUENCE: 35
atcccgcagt gacagcctaa tctacaacag tagaaattcg gatcc 45

<210> SEQ ID NO 36
<211> LENGTH: 47
<212> TYPE: DNA
<213> ORGANISM: Artificial Sequence
<220> FEATURE:
<223> OTHER INFORMATION: galK505C_18_F

<400> SEQUENCE: 36
gattaggctg tcactgcggg aatttaaata aaacgaaagg ctcagtc 47

<210> SEQ ID NO 37
<211> LENGTH: 44
<212> TYPE: DNA
<213> ORGANISM: Artificial Sequence
<220> FEATURE:
<223> OTHER INFORMATION: galK505C_18_R

<400> SEQUENCE: 37
tcccgcagtg acagcctaat ctacaacagt agaaattcgg atcc 44

<210> SEQ ID NO 38
<211> LENGTH: 47
<212> TYPE: DNA
<213> ORGANISM: Artificial Sequence
<220> FEATURE:
<223> OTHER INFORMATION: galK505C_17_F

<400> SEQUENCE: 38
agattaggct gtcactgcgg gatttaaata aaacgaaagg ctcagtc 47

<210> SEQ ID NO 39
<211> LENGTH: 43
<212> TYPE: DNA
<213> ORGANISM: Artificial Sequence
<220> FEATURE:
<223> OTHER INFORMATION: galK505C_17_R

<400> SEQUENCE: 39
cccgcagtga cagcctaatc tacaacagta gaaattcgga tcc 43

<210> SEQ ID NO 40
<211> LENGTH: 47
<212> TYPE: DNA
<213> ORGANISM: Artificial Sequence
<220> FEATURE:
<223> OTHER INFORMATION: galK505C_16_F

<400> SEQUENCE: 40
tagattaggc tgtcactgcg gatttaaata aaacgaaagg ctcagtc 47

<210> SEQ ID NO 41
<211> LENGTH: 42
<212> TYPE: DNA
<213> ORGANISM: Artificial Sequence
<220> FEATURE:
<223> OTHER INFORMATION: galK505C_16_R

<400> SEQUENCE: 41
ccgcagtgac agcctaatct acaacagtag aaattcggat cc 42

<210> SEQ ID NO 42
<211> LENGTH: 25
<212> TYPE: DNA
<213> ORGANISM: Artificial Sequence
<220> FEATURE:
<223> OTHER INFORMATION: Unedited (galK 497-517)

<400> SEQUENCE: 42
tttgtaggct gtaactgcgg gatca 25

<210> SEQ ID NO 43
<211> LENGTH: 25
<212> TYPE: DNA
<213> ORGANISM: Artificial Sequence
<220> FEATURE:
<223> OTHER INFORMATION: 510 C to A

<400> SEQUENCE: 43
tttgtaggct gtaactgagg gatca 25

<210> SEQ ID NO 44
<211> LENGTH: 25
<212> TYPE: DNA
<213> ORGANISM: Artificial Sequence
<220> FEATURE:
<223> OTHER INFORMATION: Unedited (xylB 637-657)

<400> SEQUENCE: 44
tttgttacct gaagttgcga aagcg 25

<210> SEQ ID NO 45
<211> LENGTH: 25
<212> TYPE: DNA
<213> ORGANISM: Artificial Sequence
<220> FEATURE:

<223> OTHER INFORMATION: 643 G to T

<400> SEQUENCE: 45
tttgttacct taagttgcga aagcg 25

<210> SEQ ID NO 46
<211> LENGTH: 24
<212> TYPE: DNA
<213> ORGANISM: Artificial Sequence
<220> FEATURE:
<223> OTHER INFORMATION: galK target

<400> SEQUENCE: 46
ttgtaggctg taactgcggg atca 24

<210> SEQ ID NO 47
<211> LENGTH: 24
<212> TYPE: DNA
<213> ORGANISM: Artificial Sequence
<220> FEATURE:
<223> OTHER INFORMATION: xylB target

<400> SEQUENCE: 47
ttgttacctg aagttgcgaa agcg 24

<210> SEQ ID NO 48
<211> LENGTH: 25
<212> TYPE: DNA
<213> ORGANISM: Artificial Sequence
<220> FEATURE:
<223> OTHER INFORMATION: G499 A

<400> SEQUENCE: 48
tttgtaagct gtaactgcgg gatca 25

<210> SEQ ID NO 49
<211> LENGTH: 25
<212> TYPE: DNA
<213> ORGANISM: Artificial Sequence
<220> FEATURE:
<223> OTHER INFORMATION: G499 T

<400> SEQUENCE: 49
tttgtatgct gtaactgcgg gatca 25

<210> SEQ ID NO 50
<211> LENGTH: 25
<212> TYPE: DNA
<213> ORGANISM: Artificial Sequence
<220> FEATURE:
<223> OTHER INFORMATION: G499 C

<400> SEQUENCE: 50
tttgtacgct gtaactgcgg gatca 25

<210> SEQ ID NO 51
<211> LENGTH: 25
<212> TYPE: DNA
<213> ORGANISM: Artificial Sequence
<220> FEATURE:
<223> OTHER INFORMATION: C501 A

<400> SEQUENCE: 51
tttgtaggat gtaactgcgg gatca 25

<210> SEQ ID NO 52
<211> LENGTH: 25
<212> TYPE: DNA
<213> ORGANISM: Artificial Sequence
<220> FEATURE:
<223> OTHER INFORMATION: G503 T

<400> SEQUENCE: 52
tttgtaggct ttaactgcgg gatca 25

<210> SEQ ID NO 53
<211> LENGTH: 25
<212> TYPE: DNA
<213> ORGANISM: Artificial Sequence
<220> FEATURE:
<223> OTHER INFORMATION: G503 C

<400> SEQUENCE: 53
tttgtaggct ctaactgcgg gatca 25

<210> SEQ ID NO 54
<211> LENGTH: 25
<212> TYPE: DNA
<213> ORGANISM: Artificial Sequence
<220> FEATURE:
<223> OTHER INFORMATION: T504 G

<400> SEQUENCE: 54
tttgtaggct ggaactgcgg gatca 25

<210> SEQ ID NO 55
<211> LENGTH: 25
<212> TYPE: DNA
<213> ORGANISM: Artificial Sequence
<220> FEATURE:
<223> OTHER INFORMATION: T504 A

<400> SEQUENCE: 55
tttgtaggct gaaactgcgg gatca 25

<210> SEQ ID NO 56
<211> LENGTH: 25
<212> TYPE: DNA
<213> ORGANISM: Artificial Sequence
<220> FEATURE:
<223> OTHER INFORMATION: T504 C

<400> SEQUENCE: 56
tttgtaggct gcaactgcgg gatca 25

<210> SEQ ID NO 57
<211> LENGTH: 25
<212> TYPE: DNA
<213> ORGANISM: Artificial Sequence
<220> FEATURE:
<223> OTHER INFORMATION: A505 G

<400> SEQUENCE: 57
tttgtaggct gtgactgcgg gatca 25

<210> SEQ ID NO 58
<211> LENGTH: 25
<212> TYPE: DNA
<213> ORGANISM: Artificial Sequence
<220> FEATURE:
<223> OTHER INFORMATION: A505 A

<400> SEQUENCE: 58
tttgtaggct gttactgcgg gatca 25

<210> SEQ ID NO 59
<211> LENGTH: 25
<212> TYPE: DNA
<213> ORGANISM: Artificial Sequence
<220> FEATURE:
<223> OTHER INFORMATION: A505 C

<400> SEQUENCE: 59
tttgtaggct gtcactgcgg gatca 25

<210> SEQ ID NO 60
<211> LENGTH: 25
<212> TYPE: DNA
<213> ORGANISM: Artificial Sequence
<220> FEATURE:
<223> OTHER INFORMATION: A506 T

<400> SEQUENCE: 60
tttgtaggct gtatctgcgg gatca 25

<210> SEQ ID NO 61
<211> LENGTH: 25
<212> TYPE: DNA
<213> ORGANISM: Artificial Sequence
<220> FEATURE:
<223> OTHER INFORMATION: T508 G

<400> SEQUENCE: 61
tttgtaggct gtaacggcgg gatca 25

<210> SEQ ID NO 62
<211> LENGTH: 25
<212> TYPE: DNA
<213> ORGANISM: Artificial Sequence
<220> FEATURE:
<223> OTHER INFORMATION: T508 A

<400> SEQUENCE: 62
tttgtaggct gtaacagcgg gatca 25

<210> SEQ ID NO 63
<211> LENGTH: 25
<212> TYPE: DNA
<213> ORGANISM: Artificial Sequence
<220> FEATURE:
<223> OTHER INFORMATION: T508 C

<400> SEQUENCE: 63
tttgtaggct gtaaccgcgg gatca 25

<210> SEQ ID NO 64
<211> LENGTH: 25
<212> TYPE: DNA
<213> ORGANISM: Artificial Sequence
<220> FEATURE:
<223> OTHER INFORMATION: C510 G

<400> SEQUENCE: 64
tttgtaggct gtaactgggg gatca 25

<210> SEQ ID NO 65
<211> LENGTH: 25

<212> TYPE: DNA
<213> ORGANISM: Artificial Sequence
<220> FEATURE:
<223> OTHER INFORMATION: C510 A

<400> SEQUENCE: 65
tttgtaggct gtaactgagg gatca 25

<210> SEQ ID NO 66
<211> LENGTH: 25
<212> TYPE: DNA
<213> ORGANISM: Artificial Sequence
<220> FEATURE:
<223> OTHER INFORMATION: C510 T

<400> SEQUENCE: 66
tttgtaggct gtaactgtgg gatca 25

<210> SEQ ID NO 67
<211> LENGTH: 25
<212> TYPE: DNA
<213> ORGANISM: Artificial Sequence
<220> FEATURE:
<223> OTHER INFORMATION: A639 G

<400> SEQUENCE: 67
tttgttgcct gaagttgcga aagcg 25

<210> SEQ ID NO 68
<211> LENGTH: 25
<212> TYPE: DNA
<213> ORGANISM: Artificial Sequence
<220> FEATURE:
<223> OTHER INFORMATION: A639 T

<400> SEQUENCE: 68
tttgtttcct gaagttgcga aagcg 25

<210> SEQ ID NO 69
<211> LENGTH: 25
<212> TYPE: DNA
<213> ORGANISM: Artificial Sequence
<220> FEATURE:
<223> OTHER INFORMATION: A639 C

<400> SEQUENCE: 69
tttgttccct gaagttgcga aagcg 25

<210> SEQ ID NO 70
<211> LENGTH: 25
<212> TYPE: DNA
<213> ORGANISM: Artificial Sequence
<220> FEATURE:
<223> OTHER INFORMATION: C640 A

<400> SEQUENCE: 70
tttgttaact gaagttgcga aagcg 25

<210> SEQ ID NO 71
<211> LENGTH: 25
<212> TYPE: DNA
<213> ORGANISM: Artificial Sequence
<220> FEATURE:
<223> OTHER INFORMATION: T642 G

<400> SEQUENCE: 71
tttgttaccg gaagttgcga aagcg 25

<210> SEQ ID NO 72
<211> LENGTH: 25
<212> TYPE: DNA
<213> ORGANISM: Artificial Sequence
<220> FEATURE:
<223> OTHER INFORMATION: G646 C

<400> SEQUENCE: 72
tttgttacct gaacttgcga aagcg 25

<210> SEQ ID NO 73
<211> LENGTH: 25
<212> TYPE: DNA
<213> ORGANISM: Artificial Sequence
<220> FEATURE:
<223> OTHER INFORMATION: T648 G

<400> SEQUENCE: 73
tttgttacct gaagtggcga aagcg 25

<210> SEQ ID NO 74
<211> LENGTH: 25
<212> TYPE: DNA
<213> ORGANISM: Artificial Sequence
<220> FEATURE:
<223> OTHER INFORMATION: T648 C

<400> SEQUENCE: 74
tttgttacct gaagtcgcga aagcg 25

<210> SEQ ID NO 75
<211> LENGTH: 25
<212> TYPE: DNA
<213> ORGANISM: Artificial Sequence
<220> FEATURE:
<223> OTHER INFORMATION: G649 T

<400> SEQUENCE: 75
tttgttacct gaagtttcga aagcg 25

<210> SEQ ID NO 76
<211> LENGTH: 25
<212> TYPE: DNA
<213> ORGANISM: Artificial Sequence
<220> FEATURE:
<223> OTHER INFORMATION: G649 C

<400> SEQUENCE: 76
tttgttacct gaagttccga aagcg 25

<210> SEQ ID NO 77
<211> LENGTH: 25
<212> TYPE: DNA
<213> ORGANISM: Artificial Sequence
<220> FEATURE:
<223> OTHER INFORMATION: C650 A

<400> SEQUENCE: 77
tttgttacct gaagttgaga aagcg 25

<210> SEQ ID NO 78
<211> LENGTH: 25
<212> TYPE: DNA
<213> ORGANISM: Artificial Sequence

<220> FEATURE:
<223> OTHER INFORMATION: C650 G

<400> SEQUENCE: 78
tttgttacct gaagttggga aagcg 25

<210> SEQ ID NO 79
<211> LENGTH: 26
<212> TYPE: DNA
<213> ORGANISM: Artificial Sequence
<220> FEATURE:
<223> OTHER INFORMATION: 510G insertion

<400> SEQUENCE: 79
tttgtaggct gtaactggcg ggatca 26

<210> SEQ ID NO 80
<211> LENGTH: 24
<212> TYPE: DNA
<213> ORGANISM: Artificial Sequence
<220> FEATURE:
<223> OTHER INFORMATION: 509G deletion

<400> SEQUENCE: 80
tttgtaggct gtaactcggg atca 24

<210> SEQ ID NO 81
<211> LENGTH: 27
<212> TYPE: DNA
<213> ORGANISM: Artificial Sequence
<220> FEATURE:
<223> OTHER INFORMATION: 510AG insertion

<400> SEQUENCE: 81
tttgtaggct gtaactgagc gggatca 27

<210> SEQ ID NO 82
<211> LENGTH: 23
<212> TYPE: DNA
<213> ORGANISM: Artificial Sequence
<220> FEATURE:
<223> OTHER INFORMATION: 509GC deletion

<400> SEQUENCE: 82
tttgtaggct gtaactggga tca 23

<210> SEQ ID NO 83
<211> LENGTH: 26
<212> TYPE: DNA
<213> ORGANISM: Artificial Sequence
<220> FEATURE:
<223> OTHER INFORMATION: 643A insertion

<400> SEQUENCE: 83
tttgttacct agaagttgcg aaagcg 26

<210> SEQ ID NO 84
<211> LENGTH: 24
<212> TYPE: DNA
<213> ORGANISM: Artificial Sequence
<220> FEATURE:
<223> OTHER INFORMATION: 643G deletion

<400> SEQUENCE: 84
tttgttacct aagttgcgaa agcg 24

-continued

```
<210> SEQ ID NO 85
<211> LENGTH: 27
<212> TYPE: DNA
<213> ORGANISM: Artificial Sequence
<220> FEATURE:
<223> OTHER INFORMATION: 643AG insertion

<400> SEQUENCE: 85

tttgttacct aggaagttgc gaaagcg                                    27


<210> SEQ ID NO 86
<211> LENGTH: 23
<212> TYPE: DNA
<213> ORGANISM: Artificial Sequence
<220> FEATURE:
<223> OTHER INFORMATION: 643GA deletion

<400> SEQUENCE: 86

tttgttacct agttgcgaaa gcg                                        23
```